US009802967B2

(12) United States Patent
Lai et al.

(10) Patent No.: US 9,802,967 B2
(45) Date of Patent: Oct. 31, 2017

(54) POLYMER COATED PARTICLES AND METHODS THEREOF

(71) Applicant: The University of North Carolina at Chapel Hill, Chapel Hill, NC (US)

(72) Inventors: Samuel K. Lai, Carrboro, NC (US); Qi Yang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/898,652

(22) PCT Filed: Jun. 17, 2014

(86) PCT No.: PCT/US2014/042803
§ 371 (c)(1),
(2) Date: Dec. 15, 2015

(87) PCT Pub. No.: WO2014/205000
PCT Pub. Date: Dec. 24, 2014

(65) Prior Publication Data
US 2016/0159826 A1 Jun. 9, 2016

Related U.S. Application Data

(60) Provisional application No. 61/835,953, filed on Jun. 17, 2013.

(51) Int. Cl.
*A61K 31/70* (2006.01)
*C07F 7/02* (2006.01)
*B01J 13/02* (2006.01)
*A61K 9/51* (2006.01)
*C08F 112/08* (2006.01)

(52) U.S. Cl.
CPC ............ *C07F 7/025* (2013.01); *A61K 9/5146* (2013.01); *B01J 13/02* (2013.01); *C08F 112/08* (2013.01)

(58) Field of Classification Search
USPC .......................................................... 514/34
See application file for complete search history.

(56) References Cited

U.S. PATENT DOCUMENTS

| | | | |
|---|---|---|---|
| 6,479,146 B1 | 11/2002 | Caruso et al. | |
| 2010/0266491 A1 | 10/2010 | Farokhzad et al. | |
| 2011/0182996 A1* | 7/2011 | Fukushima | A61K 47/48861 424/490 |
| 2012/0129797 A1* | 5/2012 | Akala | A61K 31/337 514/34 |
| 2013/0315937 A1* | 11/2013 | Lee | A61K 47/48046 424/179.1 |

OTHER PUBLICATIONS

Damodaran, V.B., et al. "Coformational Studies of Covalently Grafted Poly(ethylene glycol) on Modified Solid Matrices Using X-ray Photoelectron Spectroscopy," Langmuir : the ACS journal of surfaces and colloids 2010, 26, 7299-7306.

Li, S.D., et al. "Nanoparticles evading the reticuloendothelial system: Role of the supported bilayer," Biochimica et biophysica acta 2009, 1788, 2259-2266.

Budijono, S.J., et al. "Block copolymer surface coverage on nanoparticles," Colloids and Surfaces A: Physicochemical and Engineering Aspects 2010, 360, 105-110.

Woodle, M.C., et al. "Versatility in lipid compositions showing prolonged circulation with sterically stabilized liposomes," Biochimica et biophysica acta 1992, 1105, 193-200.

Fattal, E., et al. "Targeted Delivery Using Biodegradable Polymeric Nanoparticles," Fundamentals and Applications of Controlled Release Drug Delivery (Eds.: J. Siepmann, R. A. Siegel, M. J. Rathbone), Springer US, 2012, pp. 255-288.

Daigneault, M., et al. "The Identification of Markers of Macrophage Differentiation in PMA-Stimulated THP-1 Cells and Monocyte-Derived Macrophages," PloS one 2010, 5, e8668.

Lunov, O., et al. "Differential Uptake of Functionalized Polystyrene Nanoparticles by Human Macrophages and a Monocytic Cell Line," ACS nano 2011, 5, 1657-1669.

Merkel, T.J., et al. "Using mechanobiological mimicry of red blood cells to extend circulation times of hydrogel microparticles," PNAS 2011, 108, 586-591.

Jeppesen, C., et al. "Impact of Polymer Tether Length on Multiple Ligand-Receptor Bond Formation," Science 2001, 293, 465-468.

Lai, S.K., et al. "Nanoparticles reveal that human cervicovaginal mucus is riddled with pores larger than viruses," Proceedings of the National Academy of Sciences of the United States of America 2010, 107, 598-603.

Lai, S.K., et al. "Rapid transport of large polymeric nanoparticles in fresh undiluted human mucus," Proceedings of the National Academy of Sciences of the United States of America 2007, 104, 1482-1487.

Meng, F., et al. "Polyethylene glycol-grafted polystyrene particles," Journal of Biomedical Materials Research Part A. 2004, 70A, 1, 49-58.

Chen, M.Q., et al. "Graft copolymers having hydrophobic backbone and hydrophilic branches, XXIII. Particle size control of poly(ethylene glycol)-coated polystyrene nanoparticles prepared by macromonomer method," Journal of Polemer Science Part A: Polymer Chemistry, 1999, 37, 13, 2255-2166.

Korean Intellectual Property Office, International Search Report, issued in corresponding Application No. PCT/US2014/042803, dated Oct. 6, 2014.

Cu, Y., et al. Controlled surface modification with poly(ethylene)glycol enhances diffusion of PLGA nanoparticles in human cervical mucus. Mol Pharm, 2009. 6(1): p. 173-81.

(Continued)

*Primary Examiner* — Rei-Tsang Shiao
(74) *Attorney, Agent, or Firm* — Stites & Harbison, PLLC; Mandy Wilson Decker; Sean P. Ritchie

(57) ABSTRACT

Embodiments of the presently-disclosed subject matter include a composition that comprises a particle, a plurality of surface functional groups on a surface of the particle, and a plurality of coating polymers bound to the surface functional groups and forming a coating on the particle that includes a density ratio of about 0.1 to about 20.0, the density ratio being equal to a Flory radius of the plurality of coating polymers divided by a distance between adjacent surface functional groups. Embodiments of the presently-disclosed subject matter also include methods for making the present compositions as well as methods for using the present compositions to deliver a bioactive agent and treat a subject in need thereof.

17 Claims, 8 Drawing Sheets

(56) References Cited

OTHER PUBLICATIONS

Perry, J.L., et al. PEGylated Print Nanoparticles: The Impact of PEG Density on Protein Binding, Macrophage Association, Biodistribution, and Pharmacokinetics. Nano Lett, 2012. 12(10): p. 5304-10.
Jokerst, J.V., et al. Nanoparticle PEGylation for imaging and therapy. Nanomedicine (Lond), 2011 6(4): p. 715-28.
Lai, S.K., et al. Rapid transport of large polymeric nanoparticles in fresh undiluted human mucus. Proc Natl Acad Sci U S A, 2007. 104(5): p. 1482-7.
Lai, S.K., et al. Mucus-penetrating nanoparticles for drug and gene delivery to mucosal tissues. Adv Drug Deliv Rev, 2009. 61(2): p. 158-71.
Nance, E.A., et al. A dense poly(ethylene glycol) coating improves penetration of large polymeric nanoparticles within brain tissue. Sci Transl Med, 2012. 4(149): p. 149ra119.
Panorchan, P., et al. Structure-function relationship of biological gels revealed by multiple-particle tracking and differential interference contrast microscopy: the case of human lamin networks. Phys Rev E Stat Nonlin Soft Matter Phys, 2004. 70(4 Pt 1): p. 041906.
Valentine, M.T., et al. Mechanical properties of Xenopus egg cytoplasmic extracts. Biophys J, 2005. 88(1): p. 680-9.
Efremova, N.V., et al. Direct Measurement of Interactions between Tethered Poly(ethylene glycol) Chains and Adsorbed Mucin Layers. Langmuir, 2002. 18(3): p. 836-845.
Lele, B.S., et al. Mucoadhesive drug carriers based on complexes of poly(acrylic acid) and PEGylated drugs having hydrolysable PEG-anhydride-drug linkages. J. Controlled Release, 2000. 69(2): p. 237-48.
Serra, L., et al. , Design of poly(ethylene glycol)-tethered copolymers as novel mucoadhesive drug delivery systems. Eur J. Pharm. Biopharm., 2006. 63(1): p. 11-8.
Shojaei, A.H., et al. Mechanisms of buccal mucoadhesion of novel copolymers of acrylic acid and polyethylene glycol monomethylether monomethacrylate. J. Controlled Release, 1997. 47(2): p. 151-161.
Yoncheva, K., et al. Bioadhesive properties of pegylated nanoparticles. Expert. Opin. Drug Delivery, 2005. 2(2): p. 205-18.
Levin, C.S., et al. Determining the conformation of thiolated poly(ethylene glycol) on Au nanoshells by surface-enhanced Raman scattering spectroscopic assay. Anal Chem, 2006. 78(10): p. 3277-81.
Li, S.D., et al. Nanoparticles evading the reticuloendothelial system: role of the supported bilayer. Biochim Biophys Acta, 2009. 1788(10): p. 2259-66.
Duncanson, W.J., et al. Targeted binding of PLA microparticles with lipid-PEG-tethered ligands. Biomaterials, 2007. 28(33): p. 4991-9.
Jokerst, J.V., et al. Affibody-functionalized gold-silica nanoparticles for Raman molecular imaging of the epidermal growth factor receptor Small, 2011. 7(5): p. 625-33.
Wang, Y.Y., et al. Addressing the PEG mucoadhesivity paradox to engineer nanoparticles that "slip" through the human mucus barrier. Angew Chem Int Ed Engl, 2008. 47(50): p. 9726-9.
Lieleg, O., et al. Characterization of particle translocation through mucin hydrogels. Biophys J, 2010. 98(9): p. 1782-9.
Shukair, S.A., et al. Human cervicovaginal mucus contains an activity that hinders HIV-1 movement. Mucosal Immunol, 2012.
Mert, O., et al. A poly(ethylene glycol)-based surfactant for formulation of drug-loaded mucus penetrating particles. J Control Release, 2012. 157(3): p. 455-60.
Tang, B.C., et al. Biodegradable polymer nanoparticles that rapidly penetrate the human mucus barrier. Proc Natl Acad Sci U S A, 2009. 106(46): p. 19268-73.
Yang, M., et al. Biodegradable nanoparticles composed entirely of safe materials that rapidly penetrate human mucus. Angew Chem Int Ed Engl, 2011. 50(11): p. 2597-600.
Yu, T., et al. Biodegradable mucus-penetrating nanoparticles composed of diblock copolymers of polyethylene glycol and poly(lactic-<i>co</i>-glycolic acid). Drug Delivery and Translational Research, 2012. 2(2): p. 124-128.

Butterworth, M.D., et al. Preparation of ultrafine silica- and PEG-coated magnetite particles. Colloids and Surfaces A: Physicochemical and Engineering Aspects, 2001. 179(1): p. 93-102.
Kim, S., et al. Near-infrared fluorescent type II quantum dots for sentinel lymph node mapping. Nat Biotechnol, 2004. 22(1): p. 93-7.
Oussoren, C., et al. Liposomes to target the lymphatics by subcutaneous administration. Adv Drug Deliv Rev, 2001. 50(1-2): p. 143-56.
Carter, C.L., et al. Relation of tumor size, lymph node status, and survival in 24,740 breast cancer cases. Cancer, 1989. 63(1): p. 181-7.
Chambers, A.F., et al. Dissemination and growth of cancer cells in metastatic sites. Nat Rev Cancer, 2002. 2(8): p. 563-72.
Kojima, T., et al. In vivo biological purging for lymph node metastasis of human colorectal cancer by telomerase-specific oncolytic virotherapy. Ann Surg, 2010. 251(6): p. 1079-86.
Garcia-Fuentes, M., et al. Application of NMR spectroscopy to the characterization of PEG-stabilized lipid nanoparticles. Langmuir, 2004. 20(20): p. 8839-45.
Nimura, N., et al. 1-Pyrenyldiazomethane as a fluorescent labeling reagent for liquid chromatographic determination of carboxylic acids. Anal Chem, 1988. 60(19): p. 2067-70.
Jia, Z., et al. Quantitative determination of polyethylene glycol with modified Dragendorff reagent method. Desalination, 2009. 247(1-3): p. 423-429.
Merkel, T.J., et al. Using mechanobiological mimicry of red blood cells to extend circulation times of hydrogel microparticles. Proc Natl Acad Sci U S A, 2011. 108(2): p. 586-91.
Geng, Y., et al. Shape effects of filaments versus spherical particles in flow and drug delivery. Nat Nanotechnol, 2007. 2(4): p. 249-55.
Mitragotri, S., et al. Physical approaches to biomaterial design. Nat Mater, 2009. 8(1): p. 15-23.
Rizzo, V., et al. Quantitative NMR in synthetic and combinatorial chemistry. J Pharm Biomed Anal, 2005. 38(5): p. 851-7.
Daigneault, M., et al. The identification of markers of macrophage differentiation in PMA-stimulated THP-1 cells and monocyte-derived macrophages. PLoS One, 2010. 5(1): p. e8668.
Lai, S.K., et al. Privileged delivery of polymer nanoparticles to the perinuclear region of live cells via a non-clathrin, non-degradative pathway. Biomaterials, 2007. 28(18): p. 2876-84.
Jeon, S.I., et al. "Protein-Surface Interactions in the Presence of Polyethylene Oxide," J Colloid Interf Scie 1991, 142, 149-158.
Pertsin, A.J., et al. "Computer Simulation of Water near the Surface of Oligo(ethylene glycol)-Terminated Alkanethiol Self-Assembled Monolayers," Langmuir : the ACS journal of surfaces and colloids 2000, 16, 8829-8841.
Sharma, S., et al. "XPS and AFM analysis of antifouling PEG interfaces for microfabricated silicon biosensors," Biosensors & bioelectronics 2004, 20, 227-239.
Needham, D., et al. "Repulsive interactions and mechanical stability of polymer-grafted lipid membranes," Biochimica et biophysica acta 1992, 1108, 40-48.
Lasic, D.D., et al. "Sterically stabilized liposomes: a hypothesis on the molecular origin of the extended circulation times," Biochimica et biophysica acta 1991, 1070, 187-192.
Woodle, M. C., et al. "Sterically stabilized liposomes," Biochimica et biophysica acta 1992, 1113, 171-199.
Walkey, C. D., et al. "Nanoparticle Size and Surface Chemistry Determine Serum Protein Adsorption and Macrophage Uptake," Journal of the American Chemical Society 2012, 134, 2139-2147.
Allen, T.M., et al. "Liposomes containing synthetic lipid derivatives of poly(ethylene glycol) show prolonged circulation half-lives in vivo," Biochimica et biophysica acta 1991, 1066, 29-36.
Senior, J., et al. "Influence of surface hydrophilicity of liposomes on their interaction with plasma protein and clearance from the circulation: studies with poly(ethylene glycol)-coated vesicles," Biochimica et biophysica acta 1991, 1062, 77-82.
De Gennes, P.G. "Conformations of Polymers Attached to an Interface," Macromolecules 1980, 13, 1069-1075.
Perry, J.L., et al. "PEGylated Print Nanoparticles: The Impact of PEG Density on Protein Binding, Macrophage Association, Biodistribution, and Pharmacokinetics," Nano letters 2012, 12, 5304-5310.

* cited by examiner

POLYMER COATED PARTICLES AND METHODS THEREOF

RELATED APPLICATION

This application claims priority from U.S. Provisional Patent Application No. 61/835,953, filed Jun. 17, 2013, the entire disclosure of which is incorporated herein by this reference.

GOVERNMENT INTEREST

This invention was made with government support under Grant No. CA151652 awarded by the National Institutes of Health. The government has certain rights in the invention.

TECHNICAL FIELD

The presently-disclosed subject matter relates to particles comprising polymer coatings. In particular, the presently-disclosed subject matter relates to particles coated with hydrophilic polymers that can evade cells of the immune system.

INTRODUCTION

Poly(ethylene glycol) (PEG) is a flexible, neutral, and hydrophilic polymer that can create a thick, dynamic hydration shell that renders the adsorption of biomacromolecules to PEG-coated surfaces thermodynamically highly unfavorable. As a result, PEGylation reduces the aggregation of liposomes and other particles, as well as the adsorption of various serum proteins to the underlying particle core. These effects in turn decrease opsonization and clearance by the mononuclear phagocyte system (MPS), and consequently prolong the circulation kinetics of PEG-modified particles.

The grafting density necessary to achieve effective stealth properties remains not well understood. This has led to wide-ranging circulation kinetics between different PEGylated particle compositions, and achieving well-controlled PEG coatings remains challenging on many particle platforms. In addition, surface PEG grafting on polymeric particles is difficult to quantify and verify using common laboratory techniques. Thus, nanoparticle PEGylation is most often confirmed by changes in the surface charge; however, this method provides only an insensitive inference of PEG grafting density, and does not apply to inherently neutral particles. Alternative methods include nuclear magnetic resonance (NMR), thermogravimetric analysis, and fluorescence. However, these methods do not differentiate between surface and total PEG content, are not sensitive or quantitative, require specialized equipment and training, and involve the use of labels (e.g. fluorophores) that have quenching effects, can alter biological behavior, and/or cannot be readily adopted to other PEGylated systems.

Hence, there remains a need for systems and methods for quantifying and comparing PEG coatings. There also remains a need for improved systems and methods for coating particles with one or more polymers so that can evade cells.

SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

Embodiments of the presently-disclosed subject matter include compositions that comprise a particle, a plurality of surface functional groups on a surface of the particle, and a plurality of coating polymers bound to the surface functional groups and forming a coating on the particle that includes a density ratio of about 0.1 to about 20.0, the density ratio being equal to a Flory radius of the plurality of coating polymers divided by a distance between adjacent surface functional groups. In some embodiments the density ratio is greater than or equal to about 2.8, and in other embodiments the density ratio is about 2.8 to about 10.0.

To calculate the density ratio, in some embodiments the distance between adjacent surface functional groups corresponds to an average distance between at least two pairs of the surface functional groups, and in other embodiments it corresponds to a smallest distance between at least two pairs of the surface functional groups.

In some embodiments the particle includes a nanoparticle, a microparticle, or a combination thereof, and in some embodiments the particle includes a diameter of about 5 nm to about 500 nm. In some embodiments the particle is comprised of a polymer, and in some embodiments the particle includes polystyrene, silica, or combinations thereof.

In some embodiments the plurality of coating polymers include a hydrophilic polymer, and can include poly(ethylene glycol) (PEG). In some embodiments the plurality of coating polymers have a molecular weight of about 100 g/mol to about 20,000 g/mol, and in some embodiments the plurality of coating polymers have a molecular weight of about 100 g/mol to about 5,000 g/mol.

In some embodiments the plurality of coating polymers include a functional group that can react and form a bond with the surface functional groups. For example, the functional groups on the plurality of coating polymers can be selected from carboxyl, amine, aldehyde, acetal, thiol, acrylate, isocyanate, maleimide, hydroxyl, halogen, and combinations thereof. In some embodiments the functional groups are on a terminal end of the coating polymers. Likewise, in some embodiments the surface functional groups are selected from carboxyl, amine, aldehyde, acetal, thiol, acrylate, isocyanate, maleimide, hydroxyl, halogen, and combinations thereof.

Some embodiments of the present compositions can further comprise a bioactive agent.

Some embodiments of the present compositions include a plurality of the particles that include the coating polymers.

The presently-disclosed subject matter also includes methods for making a particle that comprise providing a particle that includes surface functional groups on the surface of the particle, and contacting the surface functional groups of the particle with a plurality of coating polymers to form a coating on the particle that includes a density ratio of about 0.1 to about 20.0, the density ratio being equal to a Flory radius of the plurality of coating polymers divided by a distance between adjacent surface functional groups.

Further still, the presently-disclosed subject matter also includes methods for treating a subject in need thereof that comprise administering an effective amount of a composition to a subject in need thereof, the composition including a particle, a plurality of surface functional groups on a surface of the particle, a plurality of coating polymers each bound to one of the surface functional groups and forming a coating on the particle that includes a density ratio of about 2.8 or more, the density ratio being equal to a Flory radius of the plurality of coating polymers divided by a distance between adjacent surface functional groups, and a bioactive agent.

DESCRIPTION OF EXEMPLARY EMBODIMENTS

Figure 1A:
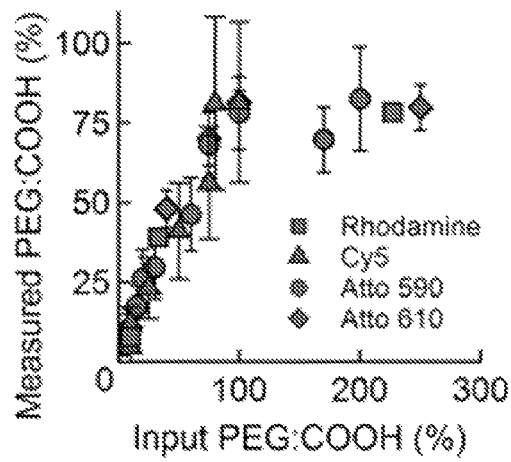
FIGS. 1A and 1A include graphs showing (FIG. 1A) the extent of PEG grafting on 100 nm polystyrene particles at various input PEG:COOH ratios directly quantified using fluorescent $NH_2$-$PEG_{5\,kDa}$, and (FIG. 1B) PEG densities on PS-$PEG_{5\,kDa}^{ATTO\,590}$ particles indirectly measured by quantifying residual COOH groups using PDAM.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Compositions

The presently-disclosed subject matter includes compositions comprising one or more particles that are coated with a coating polymer. In some embodiments, the composition comprises a particle, a plurality of surface functional groups on a surface of the particle, and a plurality of coating polymers bound to the surface functional groups and forming a coating on the particle. The coating on the particle can include a density ratio of about 0.1 to about 20.0, the density ratio being equal to a Flory radius of the plurality of coating polymers divided by a distance between adjacent surface functional groups.

In this regard, those of ordinary skill will recognize that surface functional groups on the particle can bond (graft) to a coating polymer, and the coating polymers bonded to the surface functional groups can form a polymer coating. The bonds between the surface functional groups and the coating polymers are not particularly limited and can include, but are not limited to, covalent bonds and/or ionic bonds.

The coated particles described herein can be characterized in terms of their density ratio. As mentioned above, the density ration is equal to a Flory radius ($R_F$) of the coating polymer divided by a distance between adjacent surface functional groups on the particle surface (D). The present inventors have found that the density ratio can be adjusted to form polymer coating that have certain characteristics. On the other hand, prior methods for making coated particles did not include a simple method for anticipating the characteristics of polymer coatings, but instead utilized less reliable variables such as total coating polymer content. Prior particles also did not include a simple method for characterizing polymer coatings that had been formed. Instead, prior particles were often characterized by indirectly inferring certain characteristics by measuring particle surface charge or by performing other functional assays, such as cellular uptake assays. Some prior methods attempted to characterize polymer coatings by quantifying total polymer content associated with a particle, including the polymer within the particle core and polymer at the surface of a particle, and therefore did not provide accurate measurements that correlated with the surface characteristics of coated particles. PEG was also commonly measured in terms of surface charge (i.e., ζ-potential), but this is an insensitive measure of PEG surface coverage that is greatly influenced by the particle's core material and PEG molecular weight, and the method cannot compare particles having near-neutral charges.

The prior art did not recognize that grafting polymers beyond certain threshold density ratio values can achieve dense brush conformations. Indeed, the prior art often did not recognize that polymer grafting could achieve a dense brush conformation of polymers, and instead limited grafting densities to mushroom or moderate brush conformation. In this respect, density ratios can be helpful for characterizing the in vitro and in vivo characteristics of the coated particles, among other things. Those of ordinary skill will recognize that the density ratio can be varied widely by adjusting the number of surface functional groups on a particle, the surface area of a particle, the size of a particle, the type, and the molecular weight of a coating polymer, and the like. For example, the density ratio of a coated particle can be about 0.5, 1.0, 1.5, 2.0, 2.5, 3.0, 3.5, 4.0, 4.5, 5.0, 6.0, 7.0, 8.0, 9.0, 10.0, 11.0, 12.0, 13.0, 14.0, 15.0, 16.0, 17.0, 18.0, 19.0, 20.0, or more.

The conformation of the coating polymers that form the coating is one of the characteristics that can be varied by adjusting the density ratio ($R_F/D$). The conformation of the coating polymers can then be used to determine whether a coated particle exhibits "stealth" behavior, or an ability to evade cells to a greater extent than non-coated or inadequately-coated (e.g., moderate brush) particles. Stealth behavior can allow coated particles to avoid cells of the immune system, thereby potentially increasing the circulation time (i.e., prolonged retention) of the coated particles. Stealth behavior can also include a characteristic wherein particles exhibit reduced affinity for non-target substances and cells, such as mucus or cells of the immune system. Further still, stealth behavior can refer to coated particles that exhibit greater stability in vitro and/or in vivo, potentially because the coated particles are capable of evading cells and other substances that can otherwise destabilize the structure of the particles.

Without being bound by theory or mechanism, in some instances stealth behavior can be imparted to a particle by coating the particle with a hydrophilic and/or a hydrophobic coating polymer. For instance, some embodiments of hydrophobic particles are coated with a hydrophilic coating polymer (e.g., PEG) to impart stealth characteristics to the particles in vivo. Also without being bound by theory or mechanism, in some instances stealth behavior can be imparted by providing coating polymers that have a charge. For example, embodiments of the present particles can be coated with coating polymers such that the coated particle includes a zeta-potential selected from between about −100 mV and 100 mV, between about −100 mV and 50 mV, between about −50 mV and 50 mV, between about −50 mV and 20 mV, between about −40 mV and 10 mV, between about −30 mV and 10 mV, between about −20 mV and 10 mV, or between about −10 mV and 0 mV.

In some embodiments that include a coating polymer (e.g., PEG) at relatively low grafting densities (e.g., $R_F/D \leq 1$), the coating polymer chains can adopt a diffuse "mushroom" conformation. In some embodiments with relatively higher grafting densities (e.g., $R_F/D > 1$) the coating polymer (e.g., PEG) chains can transition into a more extended "brush" conformation. In some embodiments the particles can include a "dense brush" regime when the coating polymer layer thickness exceeds $R_F$ by at least two-fold (e.g., $R_F/D \geq 2.8$), and some embodied particles that include relatively dense brush coating polymer (e.g., PEG) conformations (e.g., $R_F/D > 2.8$) exhibit effective stealth behavior. For example, some coated particles having a density ratio of greater than about 2.8 exhibit stealth behavior in the blood and mononuclear phagocyte system organs, such as the liver and spleen. This is surprising because particles in these environments generally can encounter a relatively high amount of macrophages or other immune cells that can intake and destabilize the structure of a particle. Accordingly, the density ratio described herein can be utilized to form particles that can evade cells, whereas prior quantification methods relied more on trial and error for developing satisfactory particles.

In this respect, some coating polymers can be flexible and can assume many spatial configurations. PEG is an example of a hydrophilic coating polymer that includes these characteristics. Without being bound by theory or mechanism, even when a coating polymer is grafted at densities where neighboring chains begin to overlap, there is likely periodic and frequent appearance of gaps exposing the inner particle core when two neighboring coating polymers assume an extended conformation simultaneously. Thus, known particle polymer coatings that have a high density (e.g., moderate brush conformation) can still be susceptible to intake by non-target cells. On the other hand, in embodiments of the present particles having density ratios of greater than about 2.8 the appearance of such gaps that expose a particle surface can be reduced or eliminated, thereby further enhancing the particles' ability to evade cells. Thus, embodiments of the present particles that include dense brush conformations (e.g., $R_F/D > 2.8$) present superior and unexpected results compared to the previously accepted standard of merely utilizing a coating polymer at a moderately high grafting density (e.g., $R_F/D > 1$).

Various methods can be used to measure and quantify the distance between adjacent surface functional groups (D). In some embodiments the distance between adjacent surface functional groups is calculated from the total number of surface functional groups on a particle and the particle's surface area. In other embodiments the distance between adjacent surface functional groups is equal to an average distance between at least two pairs of surface functional groups on a particle. Further still, the distance between adjacent surface functional groups can correspond to the smallest distance between at least two pairs of the surface functional groups, and in other embodiments corresponds to the smallest distance between all of the surface functional groups on a particle. The Flory radius of the coating polymers can refer to a mean Flory radius of the coating polymers that are grafted to a particle.

The presently-disclosed compositions, by providing a means to quantify and characterize a polymer coating on a particle, allow for accurate characterization and optimization of polymer-coated particles. Accurately characterizing surface coating polymers can aide in the formulation of new coated particles for specific applications (e.g., evading immune system cells), can aid in the characterization of existing polymer coated particles, or the like. In some instances the density ratio can serve as a template, whereby a user can select particles and coating polymers to achieve a predetermined density ratio that corresponds to characteristics that are desired.

Exemplary particles include any particle that can include surface functional groups, whereby the surface functional groups can be grafted with a coating polymer after the particles are formed. The term "surface functional group" as used herein refers to a moiety that can bind (graft) with a coating polymer that it contacts. Since surface functional groups are available from at surface of a substrate (e.g., particle), the substrate can substantially or wholly maintain its original structure when it binds to a coating polymer. Exemplary surface functional groups include carboxyl, amine, aldehyde, acetal, thiol, acrylate, isocyanate, maleimide, hydroxyl, halogen, or combinations thereof. Exemplary surface functional groups also include groups that are electrostatically charged. Surface functional groups can therefore bind to coating polymers via covalent bonds, ionic bonds, or both. Those of ordinary skill will appreciate other and more specific surface functional groups that can be utilized to bind a particle to a coating polymer.

The particles in some embodiments are nanoparticles. The term "nanoparticle" is used herein to refer to particles that can generally be measured on a nanometer scale and, for example, includes particles having diameters of about 1 nm, 100 nm, 200 nm, 300 nm, 400 nm, 500 nm, 600 nm, 700 nm, 800 nm, 900 nm, or 1,000 nm. Nanoparticles can also include particles being less than about 500 nm in diameter. Nanoparticle is therefore a term that can be used to describe the physical characteristics, and particularly the size, of a particle. The presently-disclosed particles can also include "microparticles," or particles measurable on a micrometer scale. Exemplary microparticles can include a diameter of about 1 μm, 2 μm, 3 μm, 4 μm, 5 μm, 6 μm, 7 μm, 8 μm, 9 μm, or 10 μm. The term particle as used herein is inclusive of at least nanoparticles and/or microparticles.

The terms "size" and "diameter" are used interchangeably herein to refer to either the physical diameter or the hydrodynamic diameter of the particles. For instance, the diameter of a substantially spherical particle may refer to the physical or hydrodynamic diameter, and the diameter of a nonspherical particle may refer to the hydrodynamic diameter. As used herein, the diameter of a non-spherical particle may refer to the largest linear distance between two points on the surface of the particle. When referring to a plurality of particles, the diameter of the particles typically refers to the mean diameter of the particles.

The particles do not have any particular compositional limitations so long as the particles comprise and/or are capable of being modified to comprise surface functional groups. In different embodiments the particles can include, but are not limited to, metals (e.g., gold particles), polymers (e.g., latex), inorganic substances (e.g., silica), or combination thereof.

Some embodiments of particles are comprised of polymers such as, but not limited to, polyamines, polyethers, polyamides, polyesters, polycarbamates, polyureas, polycarbonates, polystyrenes, polyimides, polysulfones, polyurethanes, polyacetylenes, polyetheneimines, polyisocyanates, polyacrylates, polymethacrylates, polyacrylonitriles, and polyarylates. Exemplary particles can also be comprised of cyclodextrin-containing polymers, such as cationic cyclodextrin-containing polymers, such as those described in U.S. Pat. No. 6,509,323, poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), poly(ester ethers), polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes,), derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate), and copolymers and mixtures thereof, polydioxanone and its copolymers, polyhydroxyalkanoates, poly(propylene fumarate), polyoxymethylene, poloxamers, poly(ortho)esters, poly(butyric acid), poly(valeric acid), poly(lactide-co-caprolactone), trimethylene carbonate, and polyvinylpyrrolidone.

In other embodiments the particles are comprised of the polymers described in Shieh et al., 1994, J. Biomed. Mater. Res., 28, 1465-1475 and/or U.S. Pat. Nos. 4,757,128, 5,654,381, 5,627,233, 5,628,863, 5,567,440, and 5,567,435, all of which are incorporated herein by reference. Exemplary polymers can further include polyorthoesters (e.g. as disclosed in Heller et al., 2000, Eur. J. Pharm. Biopharm., 50:121-128), polyphosphazenes (e.g. as disclosed in Vandorpe et al., 1997, Biomaterials, 18:1147-1152), and polyphosphoesters (e.g. as disclosed in Encyclopedia of Controlled Drug Delivery, pp. 45-60, Ed. E. Mathiowitz, John Wiley & Sons, Inc. New York, 1999), all of which are incorporated herein by reference. The present particles can be comprised of combinations and/or block copolymers of two or more of the polymers described herein.

The presently-disclosed subject matter is also not limited to particles, but includes any substrate that can be coated with a coating polymer. For example, the substrate may be a medical device, industrial device, or the like. Thus, the density ratios described herein can be used to make and/or characterize polymer coatings on various substrates.

The presently-disclosed coating polymers also are not particularly limited. Embodiments of coating polymers can include any of polymers described herein, including combinations and/or block copolymers of any of the polymers described herein.

In some embodiments the coating polymer is a hydrophilic polymer. In some instances, the term "hydrophilic" is used herein to refer to a molecule having a greater solubility in water than in octanol. Exemplary hydrophilic polymers include, as well as combinations and compolymers thereof. In certain embodiments the hydrophilic polymers are selected from, but are not limited to, agarose, alginic acid, amylase, amylpectin, carboxymethyl cellulose, cellularose, chitosan, collagen, dextran, fibrin, gelatin, glycogen, heparin, hyaluronic acid, glycol ethers (e.g., oligo ethylene gycol (OEG) based polymers), poly(acrylic acid) polymers, poly(methacrylic acid), poly(ethylene glycol), poly(propylene glycol), polyacrylamide, poly(vinyl alcohol), poly(vinyl acid), poly(vinyl pyrrolidone), poly(p-aminoester), poly(caprolactone), poly(glycolic acid), and combinations thereof. The hydrophilic polymers can also include linear, branched, or multi-arm forms of hydrophilic polymers. For example, hydrophilic polymers that include poly(ethylene glycol) (PEG) can include alkoxy PEG, linear PEG, bifunctional PEG, forked PEG, branched PEG, and/or pendant PEG.

Furthermore, the size of the plurality of coating polymers can affect the density ratio of a polymer coating. In some embodiments the coating polymers have a molecular weight of about 100 g/mol or more, of about 100 g/mol to about 20,000 g/mol, or about 100 g/mol to about 5,000 g/mol. In some embodiments the coating polymer can have a molecular weight of about 100 g/mol, 500 g/mol, 1,000 g/mol, 2,000 g/mol, 3,000 g/mol, 4,000 g/mol, 5,000 g/mol, 6,000 g/mol, 7,000 g/mol, 8,000 g/mol, 9,000 g/mol, 10,000 g/mol, 11,000 g/mol, 12,000 g/mol, 13,000 g/mol, 14,000 g/mol, 15,000 g/mol, 16,000 g/mol, 17,000 g/mol, 18,000 g/mol, 19,000 g/mol, 20,000 g/mol, or any value therebetween.

Embodiments of the presently-disclosed coating polymers can comprise a functional group that can react and form a bond with the surface functional groups of a particle. The functional groups on the coating polymers can be on a terminal end of the coating polymers (i.e., terminal functional group), thereby allowing the coating polymers to bind to the particle at one end and remain free at the other end. Similar to the surface functional groups, the functional groups on the coating polymers can include, but are not limited to, carboxyl, amine, aldehyde, acetal, thiol, acrylate, isocyanate, maleimide, hydroxyl, halogen, charged functional groups, and other functional groups known in the art.

In some embodiments a sufficient fraction the surface functional groups on a particle are bound to the coating polymers such that the total number of reactive functional groups on the particle is reduced. As a result, exemplary particles can be sufficiently densely coated, in some instances more than previously thought possible, and exhibit relatively little or no interaction with other substances and cells in vivo or in vitro, which, without being bound by theory or mechanism, can contribute to the stealth characteristics of a particle. In some instances at least about 25%, at least about 50%, at least about 75%, at least about 80%, or at least about 90% of the surface functional groups are bound in order to reduce the number of reactive functional groups available on the particles' surface. In some instances such results can be attained by determining the number and/or density of surface functional groups on a particle, and then grafting the particle with a corresponding number of coating polymers. Furthermore, even in some embodiments where not all of the surface functional groups are bound to a coating polymer, the density of the polymer coating can be such that the remaining free functional groups are blocked, for example by a steric effect, from contacting and/or reacting with other substances, thereby contributing to the stealth behavior of the particle.

In some embodiment the particles and/or the coating polymers are biocompatible, biodegradable, or both. The term "biocompatible" as used herein, is intended to describes a characteristic of materials that do not typically induce undesirable or adverse side effects when administered in vivo. For example, biocompatible materials may not induce side effects such as significant inflammation and/or acute rejection. It will be recognized that "biocompatibility" is a relative term, and some side effects can be expected even for some materials that are biocompatible. In some embodiments, a biocompatible material does not induce irreversible side effects, and in some embodiments a material is biocompatible if it does not induce long term side effects. One test to determine biocompatibility is to measure whether cells die upon being exposed a material in vitro. For instance, a biocompatible polymer may cause less than about 30%, 20%, 10%, or 5% cell death.

The term "biodegradable" as used herein describes a characteristic of materials that degrade under physiological conditions to form a product that can be metabolized or excreted without damage to the subject. In certain embodiments, the product is metabolized or excreted without permanent damage to the subject. Biodegradable materials can be hydrolytically degradable, can require cellular and/or enzymatic action to fully degrade, or both. Biodegradable materials also include materials that are broken down within cells. Degradation may occur by hydrolysis, oxidation, enzymatic processes, phagocytosis, or other processes. Degradation rates for materials can vary, and may be on the order of hours, days, weeks, months, or years, depending on the material.

Furthermore, the particles and/or other substrates that are coated with a plurality of coating polymers can act as a bioactive agent and/or carry a bioactive agent that provides a therapeutic benefit. For instance, some embodiments of particles are made from a substance that provides a therapeutic benefit. In other embodiments bioactive agents are contained within a particle (e.g., a micelle particle), are mixed within the particle, are attached to a surface of a particle, or a combination thereof.

The term "therapeutic benefit", "therapeutic agent", and the like are used herein to refer to the treatment of a disease or condition. In this regard, the terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative or prophylactic treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "bioactive agent" is used herein to refer to compounds or entities that alter, promote, speed, prolong, inhibit, activate, or otherwise affect biological or chemical events in a subject (e.g., a human). The manner in which the bioactive agent is incorporated into a coated particle is not particularly limited, and in some embodiments the bioactive agent can be bound to the coating polymer and/or the particle. In some embodiments the bioactive agent are encapsulated into a particle, are present at a surface of the particle, are present at a terminal end of coating polymers that oppose the particle surface, or combinations thereof. In other embodiments the bioactive agent can be comprised of the coating polymers and/or the particle. For example, bioactive agents may include, but are not limited to anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or antifungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, antisecretory factors, anticoagulants and/or antithrombotic agents, local anesthetics, ophthalmics, prostaglandins, anti-depressants, anti-psychotics, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

Embodiments particles can also comprise a targeting agent. The term "targeting agent" is used herein to refer to an agent that can selectively bind and/or is selectively attracted to a target of interest. Targeting agents may be selected from, but are not limited to, polypeptides, polynucleotides, and other functional groups. The targeting agent may or may not include a bioactive agent. The targeting agent can be attached to a surface of a particle and/or can be located on one or more coating polymers that form a coating on a particle. Accordingly, some embodiments of the present particles can be used for targeted drug (i.e., bioactive agent) delivery, and specific embodiments can be used for lymphatic drug delivery. In certain embodiments the present particles can be utilized to treat oligometastases, what may otherwise be missed by sentinel lymphadenectomy.

Further still, embodiments of the present particles can also comprise an "imaging agent," which as used herein refers to an agent that can be detected and observed by known means. Exemplary imaging agents include dyes, radioactive tags, and the like.

Some embodiments of the present compositions are biocompatible depending on the materials that comprise the particle, the coating polymers, and any other components. The term "biocompatible" as used herein describes a characteristic of materials that do not typically induce undesirable or adverse side effects when administered in vivo. For example, biocompatible materials may not induce side effects such as significant inflammation and/or acute rejection. It will be recognized that "biocompatibility" is a relative term, and some side effects can be expected even for some biocompatible materials. In some embodiments, a biocompatible material does not induce irreversible side effects, and in some embodiments a material is biocompatible if it does not induce long term side effects. One test to determine biocompatibility is to measure in vitro cell death from exposure a material. For instance, some biocompatible materials may cause less than about 30%, less than about 20%, less than about 10%, or less than about 5% cell death.

Additionally or alternatively, some embodiments of the present compositions are biodegradable depending on the materials that comprise the particle, the coating polymers, and any other components. The term "biodegradable" as used herein describes a characteristic of materials that degrade under physiological conditions to form a product that can be metabolized or excreted without damage to the subject. In certain embodiments, the product is metabolized or excreted without permanent damage to the subject. Biodegradable materials can be hydrolytically degradable, can require cellular and/or enzymatic action to fully degrade, or both. Biodegradable materials also include materials that are broken down within cells. Degradation may occur by hydrolysis, oxidation, enzymatic processes, phagocytosis, or other processes. Degradation rates for materials can vary, and may be on the order of hours, days, weeks, months, or years, depending on the material.

Pharmaceutical Compositions and Kits

The presently-disclosed subject matter also includes pharmaceutical compositions that comprise a particle, a plurality of surface functional groups on a surface of the particle, a plurality of coating polymers bound to the surface functional groups and forming a coating on the particle that includes a density ratio of about 0.1 to about 20.0, the density ratio being equal to a Flory radius of the plurality of coating polymers divided by a distance between adjacent surface functional groups, and a pharmaceutically acceptable carrier. The pharmaceutical composition can further comprise a bioactive agent. In this regard, unless stated otherwise, reference to any of the particles and compositions described herein also includes pharmaceutical compositions thereof.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of allopregnanolone to polymer and the nature of the particular polymer employed, the rate of allopregnanolone release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, such as sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The presently-disclosed subject matter further includes kits. The kits can comprise any of the particles described herein as well as a plurality of coating polymers that can bind to surface functional groups on the particles to form a polymer coating.

Methods of Making Particles

Additionally, the presently-disclosed subject matter also includes methods for making particles. Exemplary methods include providing a particle that includes surface functional groups on the surface of the particle, and contacting the surface functional groups of the particle with a plurality of coating polymers to form a coating on the particle that includes a density ratio of about 0.1 to about 20.0, the density ratio being equal to a Flory radius of the plurality of coating polymers divided by a distance between adjacent surface functional groups. The present methods can thus be performed while taking into account a density ratio of the polymer coating, and the present methods need not rely on currently employed phase separation techniques. In the present methods, any of the particles and coating particles described herein can be utilized.

The present two-step methods of providing a functionalized particle and then grafting the particle with a coating polymer can produce density ratios and/or coating polymer densities that are relatively higher than those known or achievable by the prior art. These results are superior and unexpected when compared to known coated particles and known standards for making the same.

For example, particles having surface functional groups and that are PEGylated based on the ratio of surface functional groups to PEG can permit the particles to achieve a PEG density in excess of the Flory radius. Indeed, sufficiently dense coating polymer grafting may not be achieved with polymeric particles formed by the solvent diffusion method using PEG-containing block copolymers, which is the current standard method for generating PEGylated polymeric particles. In known systems, PEG is allowed to phase separate so that it forms an exterior coating on a particle. However, as surface density of PEG increases during phase separation, bringing PEG to the surface of a particle becomes increasingly inefficient. Furthermore, since phase separation is typically conducted in the presence of a solvent, the solvent can evaporates too quickly for the PEG to sufficiently rearrange on a particle surface. Thus, some prior particles and methods for making particles fail to even achieve adequately high polymer densities (i.e., density ratios) that permit the particles to evade cells.

In some methods one can calibrate the ratio of surface functional groups on the particles to the moles and size of the coating polymer to achieve desired density ratios that impart desired (e.g., stealth) characteristics. For instance, one can select particles and coating polymers so as to achieve a density ratio greater than or equal to about 2.8 and/or a density ratio of about 2.8 to about 10.0.

Some exemplary methods also include methods for making particles that include a bioactive agent. Some methods include an additional step of providing a bioactive agent that can bind or can otherwise be incorporated into the particle, the coating polymers, or both.

Methods of Using Particles

Further still, the presently-disclosed subject matter includes methods for treating a subject in need thereof. The methods can comprise administering an effective amount of a composition to a subject in need thereof, the composition including a particle, a plurality of surface functional groups on a surface of the particle, a plurality of coating polymers each bound to one of the functional groups and forming a coating on the particle that includes a density ratio of about 2.8 or more, the density ratio being equal to a Flory radius of the plurality of coating polymers divided by a distance between adjacent surface functional groups, and a bioactive agent.

The term "administering" refers to any method of providing a composition and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can comprise topically administering the composition be submerging a tissue to be treated in a solution that includes the composition. Administration can also be accomplished by providing a device that includes the composition or pharmaceutical composition thereof, and then implanting or otherwise providing the device to a subject. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As stated above, in some embodiments a subject will be administered an "effective amount" of the particle composition, or an amount that is sufficient to achieve the desired result or to have an effect on an undesired condition. For example, an "effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compositions employed; the duration of the treatment; drugs used in combination or coincidental with the specific compositions employed and like factors well known in the medical arts. For example, it is well within the skill of the art to start doses of a compositions at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Also, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

EXAMPLES

The presently-disclosed subject matter is further illustrated by the following specific but non-limiting examples. The following examples may include compilations of data that are representative of data gathered at various times during the course of development and experimentation related to the presently-disclosed subject matter.

Example 1

This Example describes procedures performed to characterize PEG coatings on particles. In this Example, monodisperse polystyrene (PS) particles were utilized because of their well-defined densities of surface carboxylic acid groups. Thus, PEG coating densities could be varied by varying the $NH_2$:COOH ratio.

To form the coated particles, carboxylate-modified green fluorescent PS particles with mean diameters of 93 nm (Bang's Laboratories; Fishers, Ind.) and 100 nm (Invitrogen; Carlsbad, Calif.) were obtained. The surface COOH densities of the particles (2.1 and 5.1 COOH/nm² for 93 and 100 nm particles, respectively) were calculated from the mEq/g values provided by the manufacturers. Several MW methoxy PEG amine ($NH_2$-PEG) were obtained, including 2 and 5 kDa in MW (Rapp Polymere; Tuebingen, Germany), 10 kDa and 20 kDa (JenKem; Allen, Tex.), and 207, 383, and 559 Da (ThermoScientific; Waltham, Mass.). $NH_2$-PEG was conjugated to the PS particles be washing the particles thrice with MilliQ $H_2O$ and resuspended in 50 mM borate buffer (pH 7.8). Methoxy PEG amine was added to the PS particles at varying PEG:COOH ratios, and 1-ethyl-3-(3-dimethylaminopropyl)carbodiimide (EDC, Invitrogen) and N-hydroxysulfosuccinimide (S-NHS, ThermoScientific) were added at five-fold molar excess of PEG. The EDC/S-NHS reaction was allowed to proceed overnight at room temperature. The reaction mixture was quenched with excess glycine, and the PEG-modified particles were washed with MilliQ $H_2O$ and resuspended in water to stock concentrations (~10-20 mg/mL). The hydrodynamic size and $\zeta$-potential of the synthesized particles were determined by dynamic light scattering and laser Doppler anemometry, respectively, using a Zetasizer Nano (Malvern, UK).

Fluorescent PEG was used to directly quantify the PEG grafting density. The procedures utilized rhodamine B and Cy5 PEG amine (5 kDa) (NanoCS; New York, N.Y.) as well as maleimide ATTO 590 and ATTO 610 (Sigma-Aldrich; St. Louis, Mo.). The fluorophores were conjugated in excess onto thiol PEG amine (5 kDa, JenKem) via overnight incubation at room temperature in PBS/methanol (80%/20%) or PBS. Unreacted dye was removed using an Amicon Ultra-0.5 mL filter device MWCO 3 kDa (Millipore; Billerica, Mass.). The different fluorescent PEG amines (5 kDa) were mixed with methoxy PEG amine at a 1:4, 1:20, or 1:40 ratio, followed by conjugation to PS particles at various total PEG:COOH ratios. The fluorescence of the PS-PEG Rhodamine B, Cy5, ATTO 590, and ATTO 610 particles were measured at 570/595, 645/675, 590/625, and 610/640 nm, respectively, using a SpectraMax 2 microplate reader (Molecular Devices; Sunnyvale, Calif.). Sample fluorescence was compared to a standard curve generated using free PEG-fluorophores to quantify the number of conjugated fluorescent PEG groups and the effective total PEG grafting.

The residual carboxylic groups present on the PS-PEG particles were quantified using 1-pyrenyldiazomethane (PDAM; Invitrogen). The PS-PEG particles (1 μL) were diluted in 20 μL of Pluronic F127 solution (15 mg/mL) in a half-area black 96 well plate. Ten microliters of a saturated PDAM solution (~0.3 mg/mL in methanol) were added to each well, and the PDAM and particle fluorescence intensities were measured at 340/395 and 480/520 nm, respectively, using a SpectraMax 2 microplate reader. The sample PDAM fluorescence was compared to a standard curve of unmodified PS particles to determine the residual carboxylic group density (% COOH). The density of conjugated PEG groups (P) was calculated as follows:

$$P = C \times (100 - \% \text{ COOH}) \quad (1)$$

where C is the density of COOH groups present on the unmodified PS particle. Duplicate samples were tested per run, and the grafting estimates reflect an average of at least three independent experiments. To confirm the PDAM assay results, non-fluorescent PS particles (110 nm diameter; Bang's Laboratories) modified with PEG ATTO 590 at varying PEG:COOH ratios were analyzed using the PDAM assay, and the indirectly estimated PEG density was compared to the PEG density directly quantified using ATTO 590 fluorescence.

The Flory radius, $R_F$, and grafting density, D, were determined using the following equations:

$$R_P = \alpha N^{3/5} \quad (2)$$

$$A = \frac{1}{p} \quad (3)$$

$$D = 2\sqrt{\frac{A}{\pi}} \quad (4)$$

where α is the monomer length of PEG (0.35 nm), N the number of PEG repeats, and A the area occupied per PEG chain. For the purposes of this Example, the mushroom and brush conformations were defined by $R_F/D \leq 1$ and $R_F/D > 1$, respectively. The dense brush conformation was considered to occur when the thickness of the PEG layer (L) exceeds the $R_F$ by two-fold (i.e., when $R_F/D > 2.8$).

$$L = \frac{N\alpha^{5/3}}{D^{2/3}} \quad (5)$$

Group comparisons were performed using one-way ANOVA, followed by Tukey's post hoc test, on SAS 9.3 software. A p-value<0.05 was considered to indicate statistical significance. All data are presented as mean±S.D.

The results of this analysis of the PS particles are shown below in Table 1.

residual COOH content on PS-PEG particles using fluorogenic 1-pyrenylyldiazomethane (PDAM, MW 242.3; FIG. 1B). Based on these procedures, it was determined that graft density could be measured for the PS-PEG particles grafted with only methoxy PEG amine, eliminating the need to use fluorophores. The elimination of the terminal fluorophores groups also eliminated any possible influence of fluorophore on particle interactions with immune cells.

Example 2

Using the particles described in Example 1, this Example describes procedures conducted to characterize whether PEG coated PS particles can evade cells, and particularly cells of the immune system. Human monocytic THP-1 cells were obtained (University of North Carolina at Chapel Hill tissue culture facility) and were maintained at $5 \times 10^5$ cells/mL in RPMI 1640 medium containing 10% fetal bovine serum and 1× penicillin-streptomycin, with incubation at 37° C. and 5% $CO_2$. THP-1 cells were seeded into 24 well plates at $1.70 \times 10^5$ cells/mL were differentiated in culture medium containing 200 nM phorbol 12-myristate 13-acetate (PMA; Sigma-Aldrich). The PMA-containing medium was removed 3 d later and replaced with fresh culture medium,

TABLE 1

Particle size, ζ-potential, PEG density, and theoretical $R_F/D$ values for the PEGylated particles.

| PS Particle Size (d. nm) | PEG MW (Da) | PEG Density (PEG/nm²) | Particle Size (d. nm) | ζ-potential (mV) | $R_F/D$ | PEG Conformation |
|---|---|---|---|---|---|---|
| 93 | — | 0.0 ± 0.2 | 95 ± 2 | −48 ± 2 | — | — |
| 100 | — | 0.0 ± 0.1 | 109 ± 4 | −55 ± 5 | — | — |
| 93 | 207 | 1.1 ± 0.2 | 120 ± 6 | −7 ± 13 | 0.8 | mushroom |
| 93 | 207 | 1.3 ± 0.1 | 96 ± 1 | 9 ± 5 | 0.9 | mushroom |
| 100 | 207 | 4.1 ± 0.5 | 121 ± 7 | 18 ± 3 | 1.6 | brush |
| 93 | 383 | 0.2 ± 0.2 | 112 ± 11 | −27 ± 2 | 0.5 | mushroom |
| 93 | 383 | 1.3 ± 0.2 | 106 ± 6 | 9 ± 4 | 1.3 | brush |
| 100 | 383 | 4.4 ± 0.2 | 129 ± 23 | 16 ± 3 | 2.4 | brush |
| 93 | 559 | 0.2 ± 0.2 | 97 ± 1 | −36 ± 4 | 0.6 | mushroom |
| 93 | 559 | 0.5 ± 0.2 | 112 ± 10 | −6 ± 5 | 1.0 | brush |
| 93 | 559 | 1.4 ± 0.1 | 99 ± 5 | 9 ± 3 | 1.7 | brush |
| 100 | 559 | 3.6 ± 0.5 | 133 ± 11 | 7 ± 1 | 2.7 | brush |
| 93 | 2 kDa | 0.2 ± 0.1 | 101 ± 3 | −38 ± 8 | 1.3 | brush |
| 93 | 2 kDa | 0.8 ± 0.3 | 107 ± 3 | −2 ± 2 | 2.7 | brush |
| 93 | 2 kDa | 1.3 ± 0.1 | 128 ± 6 | −5 ± 8 | 3.5 | dense brush |
| 93 | 2 kDa | 1.4 ± 0.2 | 105 ± 3 | −2 ± 4 | 3.6 | dense brush |
| 93 | 2 kDa | 1.6 ± 0.1 | 139 ± 18 | 1 ± 3 | 3.9 | dense brush |
| 100 | 2 kDa | 4.2 ± 0.2 | 141 ± 4 | 1 ± 1 | 6.3 | dense brush |
| 93 | 5 kDa | 0.1 ± 0.2 | 108 ± 8 | −46 ± 5 | 2.0 | brush |
| 93 | 5 kDa | 0.2 ± 0.2 | 105 ± 5 | −45 ± 3 | 2.6 | brush |
| 93 | 5 kDa | 0.6 ± 0.2 | 105 ± 1 | 4 ± 7 | 4.2 | dense brush |
| 93 | 5 kDa | 0.8 ± 0.2 | 110 ± 3 | −2 ± 3 | 4.7 | dense brush |
| 93 | 5 kDa | 0.9 ± 0.2 | 109 ± 2 | −4 ± 2 | 5.1 | dense brush |
| 93 | 5 kDa | 1.2 ± 0.2 | 108 ± 1 | 1 ± 3 | 5.8 | dense brush |
| 93 | 5 kDa | 1.5 ± 0.2 | 135 ± 9 | 0 ± 2 | 6.6 | dense brush |
| 100 | 5 kDa | 3.6 ± 0.1 | 134 ± 6 | −1 ± 1 | 10.1 | dense brush |
| 93 | 10 kDa | 0.4 ± 0.1 | 113 ± 3 | −2 ± 1 | 5.3 | dense brush |
| 93 | 10 kDa | 1.2 ± 0.1 | 116 ± 1 | −0 ± 3 | 8.8 | dense brush |
| 93 | 10 kDa | 1.5 ± 0.1 | 135 ± 6 | 0 ± 4 | 9.7 | dense brush |
| 100 | 10 kDa | 3.0 ± 0.2 | 134 ± 5 | −0 ± 1 | 13.9 | dense brush |
| 93 | 20 kDa | 0.1 ± 0.1 | 100 ± 2 | −46 ± 2 | 4.6 | dense brush |
| 93 | 20 kDa | 1.4 ± 0.2 | 136 ± 5 | −0 ± 1 | 14.3 | dense brush |
| 100 | 20 kDa | 2.4 ± 0.1 | 147 ± 4 | 1 ± 2 | 18.9 | dense brush |

Figure 1B:
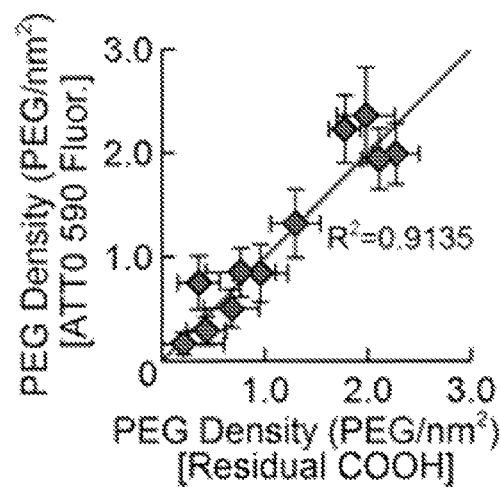
Figure 2A:
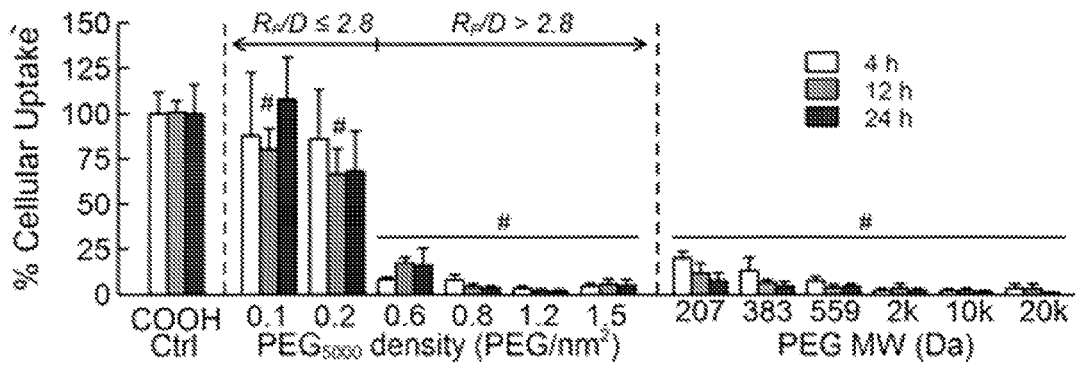
FIGS. 2A to 2C include (FIG. 2A) a graph showing the uptake of PEG-coated particles with various grafting densities and PEG molecular weights (MWs) by differentiated human THP-1 cells quantified using flow cytometry, (FIG. 2B) a phase diagram mapping particle uptake by differentiated THP-1 cells at 4 h as a function of PEG length (MW) and coating density (PEG groups/$nm^2$), and (FIG. 2C) a graph showing the uptake of various PEG-coated particles by primary human immune cells quantified by flow cytometry. The data represents at least n=3 independent experiments performed in triplicate. # indicates P<0.01 vs. control PS particles.
Figure 2B:
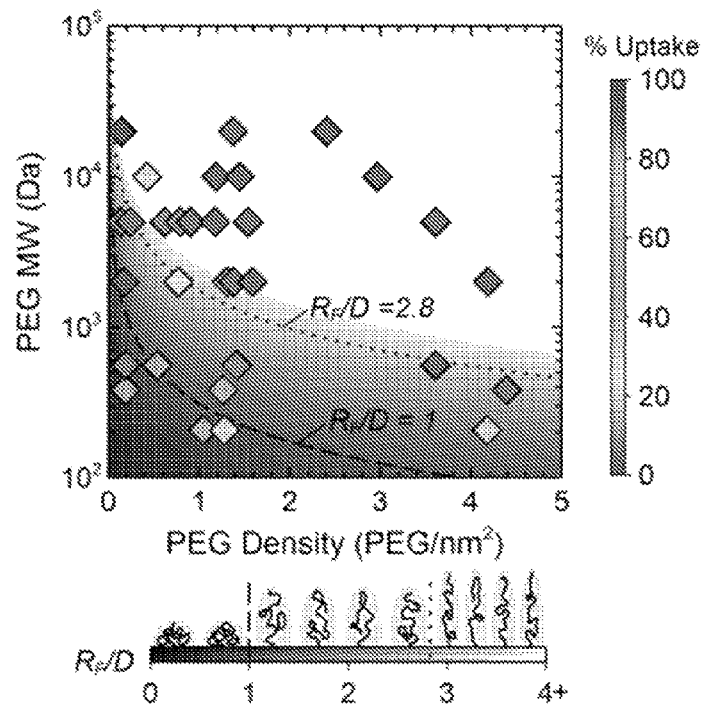

Some of the facilitated PEG grafts had densities exceeding the minimum defined for brush and even dense brush conformations (FIGS. 1A and 2B). PEG grafting was verified using fluorescently labeled PEG chains, which showed very dense PEG grafting with four different PEG-fluorophore conjugates. The direct quantitation was correlated to PEG densities indirectly measured by quantitating the followed by incubation with carboxylate PS or PS-PEG particles at a $1:10^4$ cell-to-particle ratio for 4, 12, or 24 h. Flow cytometry was performed using a FACSCanto instrument (BD; Franklin Lakes, N.J.), and propidium iodide (Invitrogen) staining was used for live/dead cell determination. At least 10,000 events were recorded per sample, and the data were analyzed using BD FACSDiva software. The data represents n=3 independent experiments performed in triplicate.

Furthermore, individual human buffy coat units were obtained (Innovative Research; Novi, Mich.). The peripheral blood mononuclear and polymorphonuclear cells were collected by Ficoll-Paque Premium separation and were resuspended at $3 \times 10^6$ cells/mL in RPMI 1640 medium containing 25 mM HEPES, 1× penicillin-streptomycin, 1× sodium pyruvate, 0.1% β-mercaptoethanol, and 10% human serum. Leukocytes were seeded in 96 well plates and incubated with carboxylate PS or PS-PEG particles at a $1:10^4$ cell-to-particle ratio for 4 or 24 h, with incubation at 37° C. and 5% $CO_2$ and shaking at 200 rpm. After detachment with trypsin and washing with cold PBS, the cells were incubated with Fc block for 5 min on ice (eBioscience). For the detection of cell surface markers, monoclonal mouse anti-human antibodies $IgG1_\kappa$ CD56 APC-eFluor™ 780, CD16 APC, or CD14 APC-eFluor® 780 (eBioscience); $IgM_\kappa$ CD66b PerCP-Cy5.5 (BD); or $IgG1_\kappa$ CD3 APC (Invitrogen) or CD19 PE were incubated with the cells for 20 min in the dark on ice. SYTOX® Blue dead cell stain (Invitrogen) was added prior to cell analysis for live/dead cell determination. Flow cytometry was performed using a Dako CyAn instrument (Beckman-Coulter; Brea, Calif.). At least 50,000 events were recorded per sample, and the data were analyzed using Kaluza software (Beckman-Coulter). The data represents n=3 independent experiments performed in triplicate.

Figure 2C:
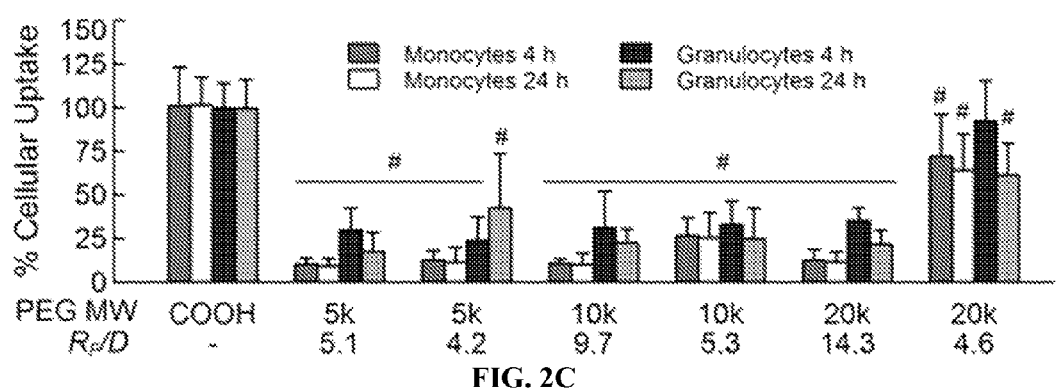
Figure 3A:
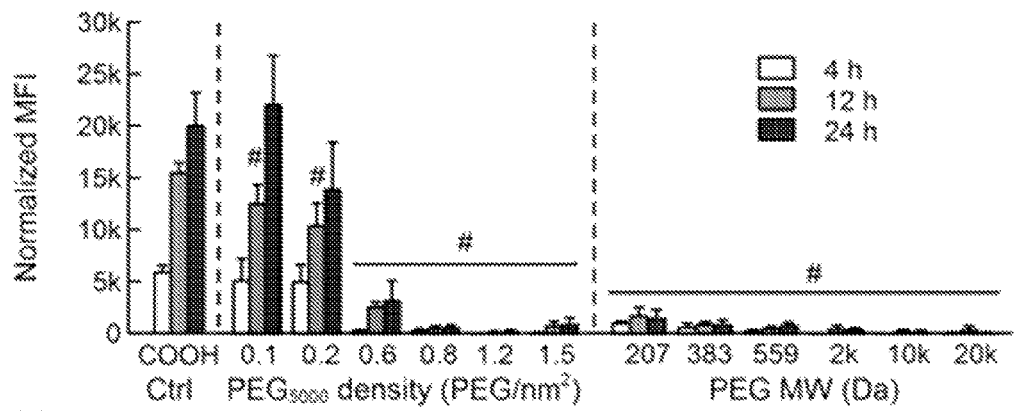
FIGS. 3A to 3C include graphs showing uptake of PEG-coated particles with various grafting densities and PEG MW by (FIG. 3A) differentiated human THP-1 cells and (FIG. 3B) primary human monocytes and granulocytes, wherein the data represent n=3 independent experiments performed in triplicate (# indicates P<0.01 vs. control PS particles), and (FIG. 3C) shows flow cytometry histograms for the untreated, unmodified polystyrene (PS), and PS-PEG (5 kDa, 0.91 PEG/$nm^2$) groups with various primary leukocyte populations.
Figure 3B:
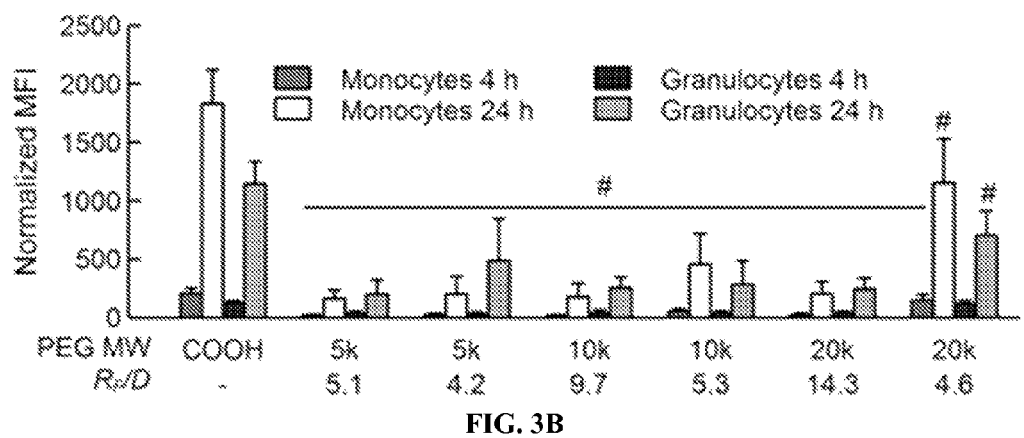
Figure 3C:
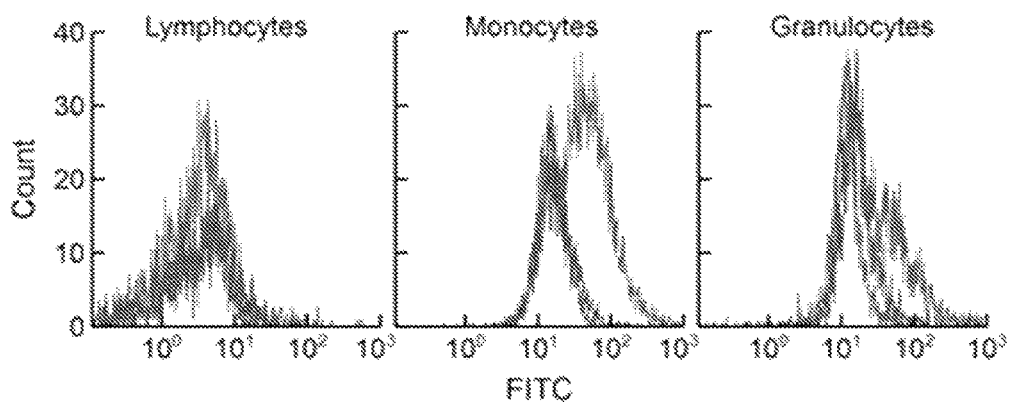

For particles coated with different amounts of 5 kDa PEG, uptake by differentiated THP-1 cells, a human macrophage-like cell line, was effectively suppressed for at least 24 h with grafting densities≥0.8 $PEG/nm^2$ ($R_F/D \geq 4.7$; FIGS. 2A and 3(A-C)). With PEG MW (range: 207 Da-20 kDa) at grafting densities exceeding 1.2 $PEG/nm^2$ ($R_F/D > 3.6$ except 559 Da PEG, where $R_F/D = 1.7$), it was found that even very short PEGs (≤12 subunit repeats, or 559 Da) were able to reduce uptake at these high grafting densities. To correlate the observed cell uptake to the theoretical PEG conformational regime, a phase diagram of particle uptake as a function of PEG MW and grafting density was developed (FIG. 2B). Effective suppression of immune cell uptake occurred with dense brush PEG at surface densities exceeding the mushroom-brush transition. Nearly all of the formulations that exhibited a >20-fold reduction in THP-1 uptake compared to uncoated particle control possessed PEG coatings with $R_F/D$ values in excess of 2.8. For longer PEG chains (≥10 kDa), a relatively high PEG density ($R_F/D > 8$) maximally reduce immune cell uptake. For a wide range of PEG MW, PEGylated particles with $R_F/D > 2.8$ also exhibited reduced uptake by primary human peripheral leukocytes (FIG. 2C).

Example 3

Again, using the PS particles described in Example 1, this Example characterizes the behavior of the PEG coated particles in vivo. Female BALB/c mice (20-24 g body weight) were obtained (Charles River Laboratories; Wilmington, Mass.). The mice were anesthetized with isoflurane, and a tail vein catheter was inserted. After the hair was removed from the left ear, the mice were placed onto a heated stage (37° C.) in a prone position with the left ear immobilized by taping onto an aluminum block. The vasculature was located manually on an IV 100 Olympus laser scanning microscope by the detection of green autofluorescence from red blood cells under white light excitation. A suspension of green fluorescent PS or PS-$PEG_{5\ kDa}$ particles (300 μg/20 g mouse, n=3-4 per group) in a total of 100 μL PBS was slowly injected via the catheter, followed by a 50 μL flush of PBS and imaging with a 488 nm laser for 2 h at 5 s intervals. To analyze the particle blood circulation, the image files from each scan were exported to ImageJ, and the images were stacked in groups of four. For each sample scan, the region of interest containing the vasculature was analyzed for the fluorescent signal. If needed, a correction for variation in laser intensity or drift was performed by background correcting each image to the signal from a vasculature-free region of the scan. The data were exported to GraphPad Prism for area under the curve (AUC) analysis.

After 2 h, the mice were sacrificed, and tissues (heart, liver, kidneys, spleen, lungs) were collected. Blood was also collected by cardiac puncture and added in 100 μL aliquots to a black 96 well plate. The tissues from treated and untreated animals were imaged using an IVIS Kinetic fluorescence imaging system with excitation at 465 nm. The fluorescent signal present in the tissues was calculated as a percentage of the total recovered fluorescence for the collected tissue samples. The fluorescence of particles in the blood was measured using a SpectraMax 2 microplate reader and compared to a standard curve generated using green fluorescent PS particles added to untreated blood.

Additional mice (n=4 per group) were injected with densely PEGylated particles (5 kDa PEG, 3.61 $PEG/nm^2$; 300 μg/20 g mouse) in a total of 100 μL PBS via the tail vein, and the mice were sacrificed at various time points (0, 12, 24, and 48 h). Tissues (heart, liver, kidneys, spleen, lungs) and blood were collected, and the tissue distribution and particle concentration in the blood were determined. PK analysis of the blood concentration data was conducted with PKSolver; one- and two-compartment models were fit to the data to determine the best fit.

Figure 4A:
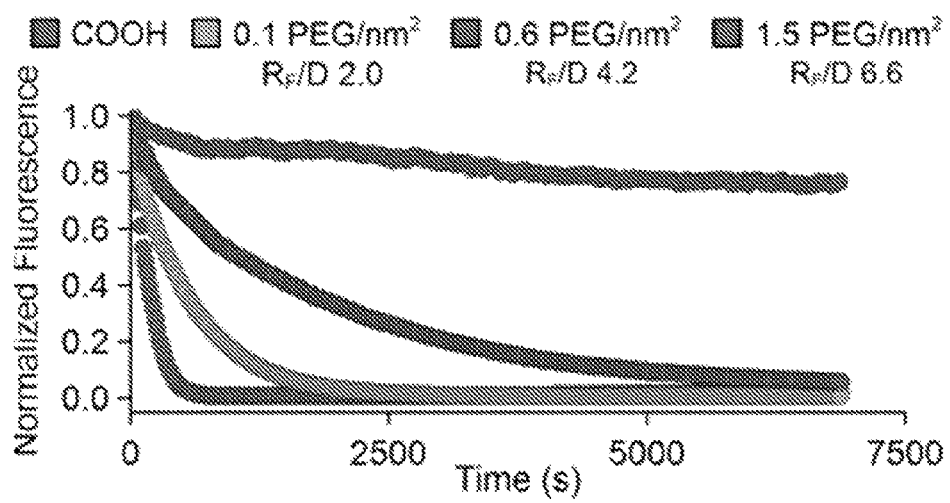
FIGS. 4A to 4C include graphs showing (FIG. 4A) the blood circulation profiles of PS and various PS-$PEG_{5\,kDa}$ particles observed using intravital microscopy, (FIG. 4B) the biodistribution of the different formulations 2 h after intravenous injection, and (FIG. 4C) the blood circulation profile of PEGylated particles with $R_F/D \geq 6.5$ over extended times (n=4), wherein the dashed line represents the fit for a two-compartment model.
Figure 4B:
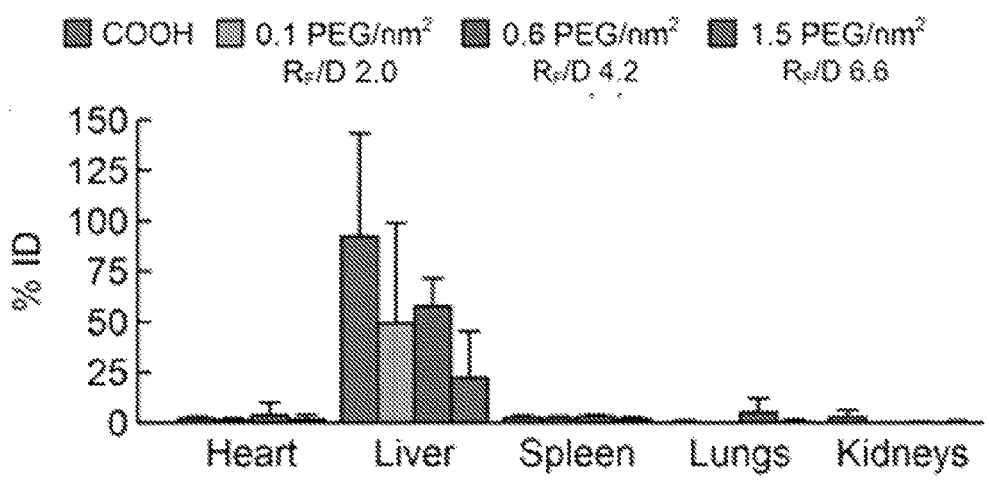
Figure 4C:
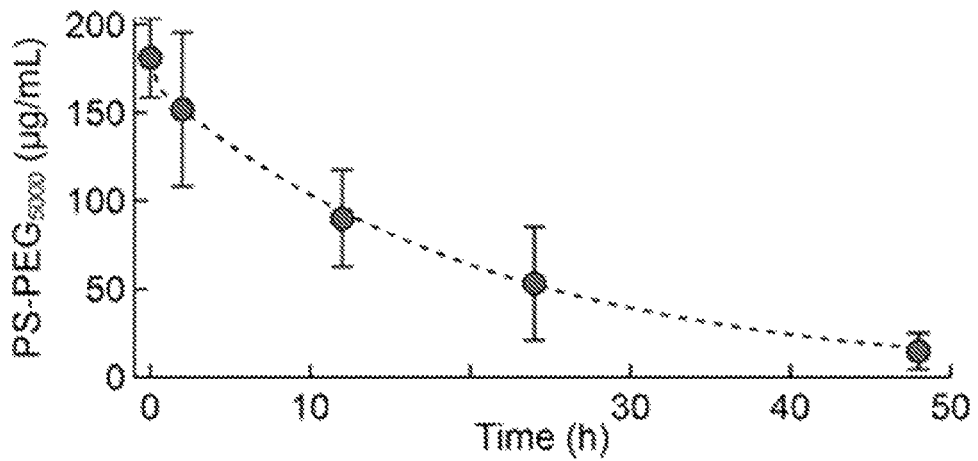
Figure 5:
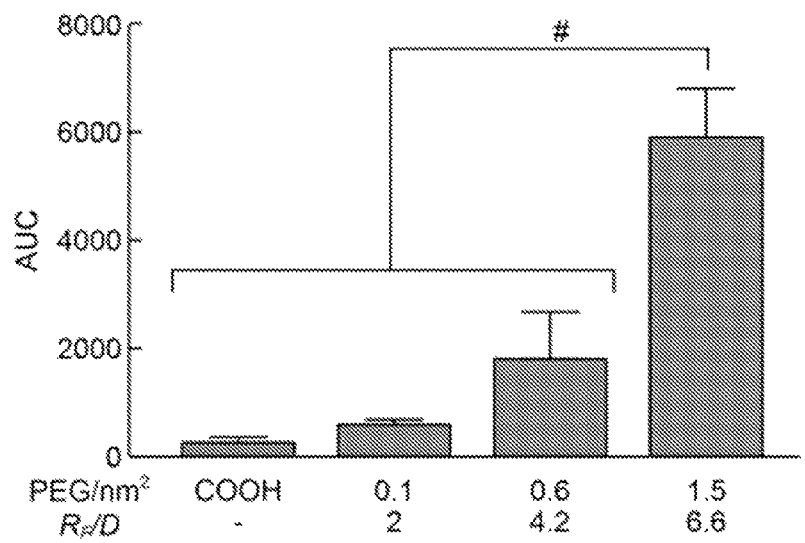
FIG. 5 includes a graph showing the area under the curve plot for the blood profiles of PS and various PS-$PEG_{5\,kDa}$ particles observed using intravital imaging. The data represent n=3-4 independent animals (# indicates P<0.01).
Figure 6:
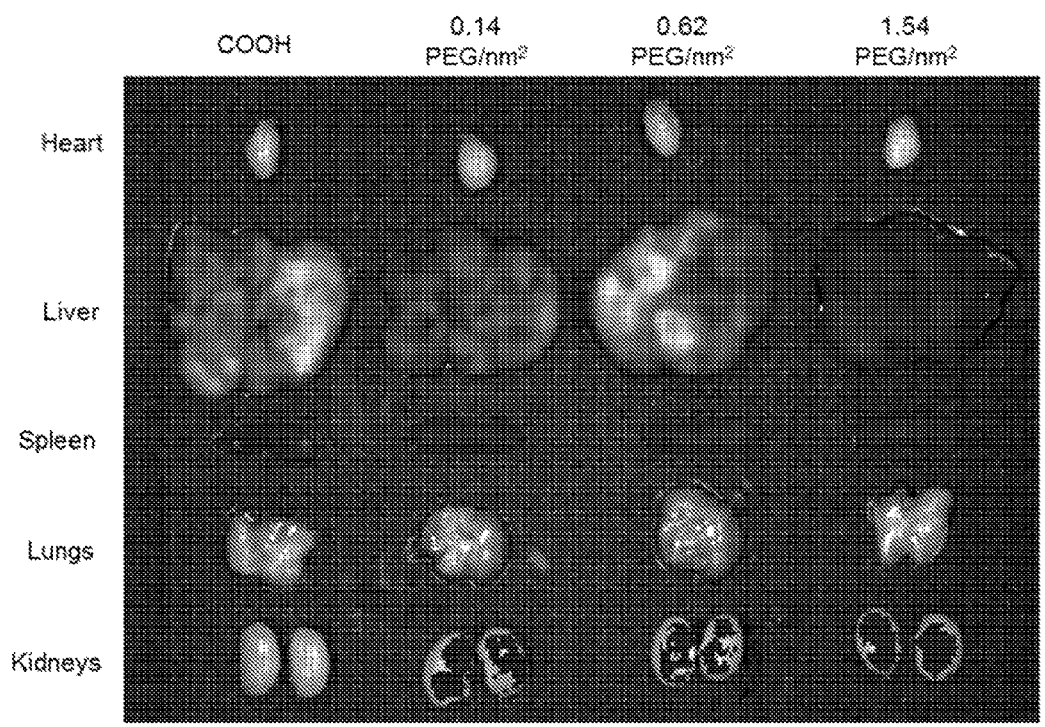
FIG. 6 includes fluorescence images of organs collected at 2 h from BALB/c mice dosed with PS or PS-$PEG_{5\,kDa}$ particles.
Figure 7A:
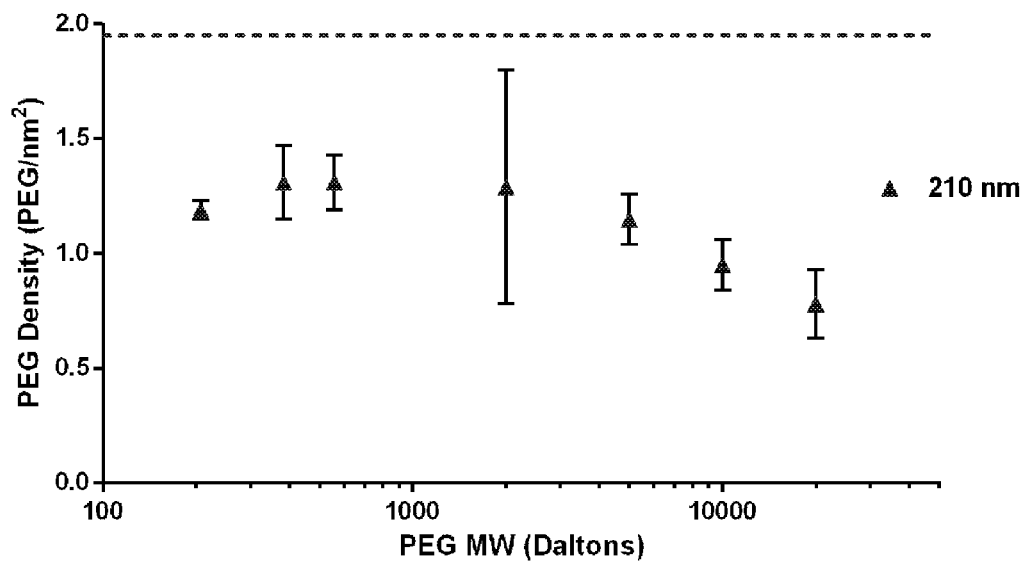
FIGS. 7A to 7C include graphs showing the modification of (FIG. 7A) a 210 nm particle with PEG of varying sizes, (FIG. 7B) 93 and 100 nm particles with PEG of varying sizes, and (FIG. 7C) particles of varying sizes with $PEG_{2k}$, wherein the dashed lines correspond to the maximum theoretical modification for each particle.
Figure 7B:
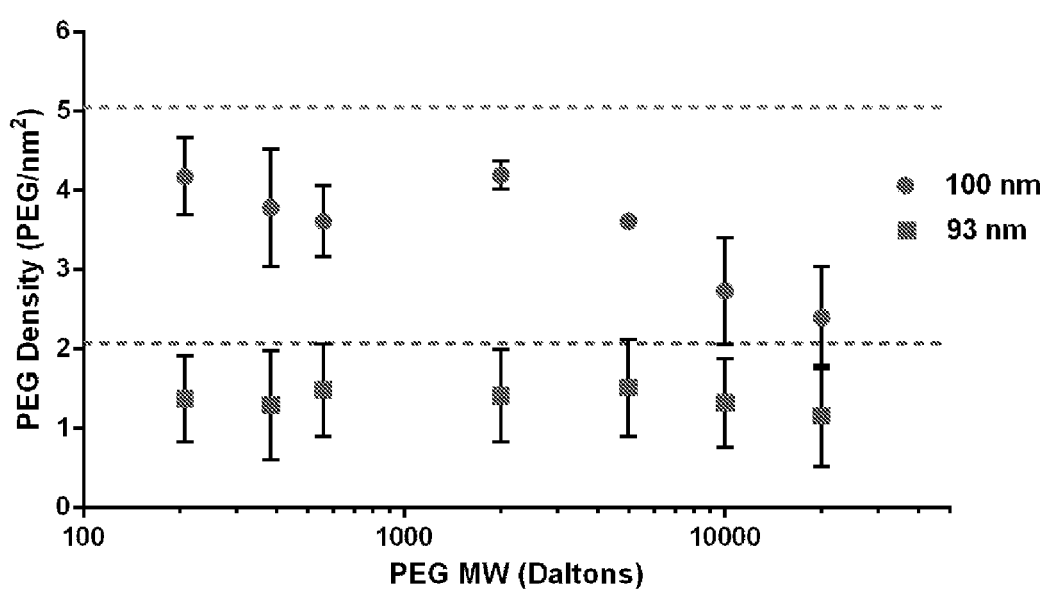
Figure 7C:
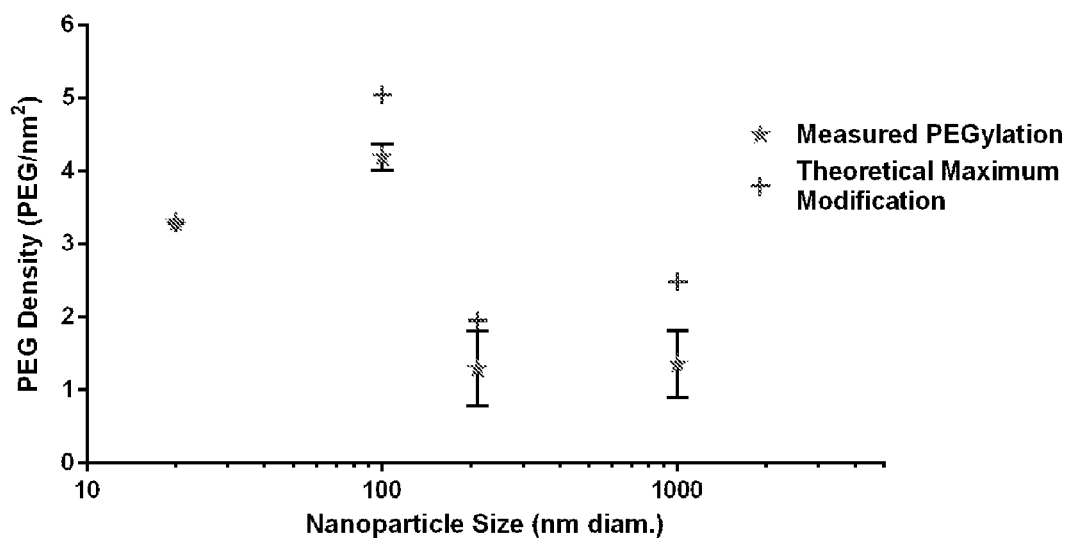
Figure 8:
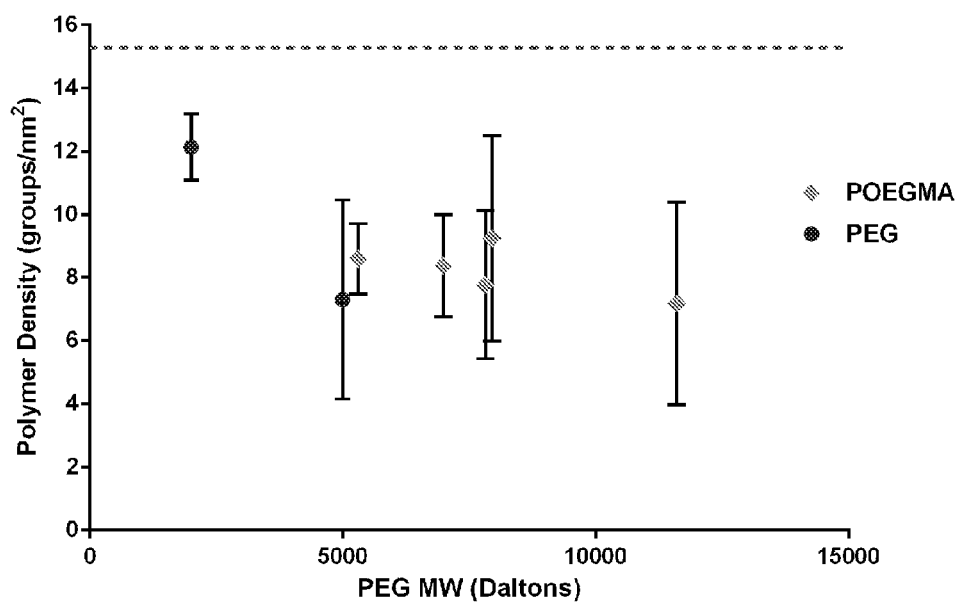
FIG. 8 includes a graph showing the modification of 500 nm PS particles by PEG and POEGMA coating polymers of varying sizes. The maximum theoretical modification is indicated by the dashed line.

It was observed that prolonged circulation of solid polymeric nanoparticles in vivo increased when PEG was grafted beyond the minimum for a dense brush regime. Particles coated with ≥1.5 $PEG/nm^2$ ($R_F/D \geq 6.5$) were able to effectively evade clearance and persist in systemic circulation (<20% cleared after 2 h). In contrast, some of the particles with slightly less dense PEG coatings, even those at brush or dense brush regimes ($R_F/D=2.0$ and 4.2), were eliminated within 2 h, presumably by the MPS cells in the liver (FIGS. 4(A,B), 5, and 6). The reduced PEG blood clearance at 2 h directly translated to prolonged circulation times in excess of 24 h (FIG. 4C). The best-fit two-compartment model yielded an elimination half-life of 14.3 h for the high density PEGylated particles (Table 2).

TABLE 2

PK model and parameters for various PS-$PEG_{5\ kDa}$ particles (n = 3-4).

| PEG Density (PEG/nm²) | $R_F/D$ | Best-fit Model | $R^2$ | $t_{1/2}$ (h) | CL (mL/h) | $AUC_{0-t}$ (μg/mL * h) | $V_D$ (mL) |
|---|---|---|---|---|---|---|---|
| COOH | — | One-compartment | 0.991 | 0.03 | — | — | — |

TABLE 2-continued

PK model and parameters for various PS-PEG$_{5 kDa}$ particles (n = 3-4).

| PEG Density (PEG/nm$^2$) | R$_F$/D | Best-fit Model | R$^2$ | t$_{1/2}$ (h) | CL (mL/h) | AUC$_{0-t}$ (μg/mL * h) | V$_D$ (mL) |
|---|---|---|---|---|---|---|---|
| 0.1 | 2.0 | One-compartment | 0.995 | 0.11 | — | — | — |
| 0.6 | 4.2 | Two-compartment | 0.992 | 0.27 (t$_{1/2,\alpha}$), 0.75 (t$_{1/2,\beta}$) | — | — | — |
| 3.6 | 10.1 | Two compartment | 0.999 | 0.13 (t$_{1/2,\alpha}$), 14.34 (t$_{1/2,\beta}$) | 0.086 | 3.13 | 1.66 |

Example 4

This Example describes procedures performed to grafting PEG coatings on silica particles. Thus, this Example demonstrates that the presently-disclosed subject matter is applicable to a wide variety of materials and applications. To avoid undue repetition, some steps that are repeated from the prior Examples are omitted in this Example.

Carboxylate-modified silicon dioxide (Si) nanoparticles (500 and 700 nm diameter; Corpuscular, Cold Spring, N.Y., USA) were conjugated with methoxy PEG amine (2 and 5 kDa MW; Rapp Polymere) according to the following protocol. The Si nanoparticles were washed twice with 50 mM MES buffer, pH 6.0, and then redispersed in the MES buffer. The Si particles were pre-incubated for 10 min with EDC at 20-fold molar excess of the Si COOH groups, and then N-hydroxysuccinimide (NHS; ThermoScientific) was added at 20-fold molar excess of the Si COOH groups. Methoxy PEG amine was mixed with the activated Si particles at excess PEG:COOH ratios (3× or higher). The EDC/NHS reaction was allowed to proceed overnight at room temperature, and then the PEG-modified particles were washed with MilliQ H$_2$O and resuspended in water to stock concentrations (~25 mg/mL). The hydrodynamic size and ζ-potential of the synthesized particles in 10 mM NaCl buffer were determined by dynamic light scattering and laser Doppler anemometry, respectively, using a Zetasizer Nano (Malvern, UK).

Figure 9:
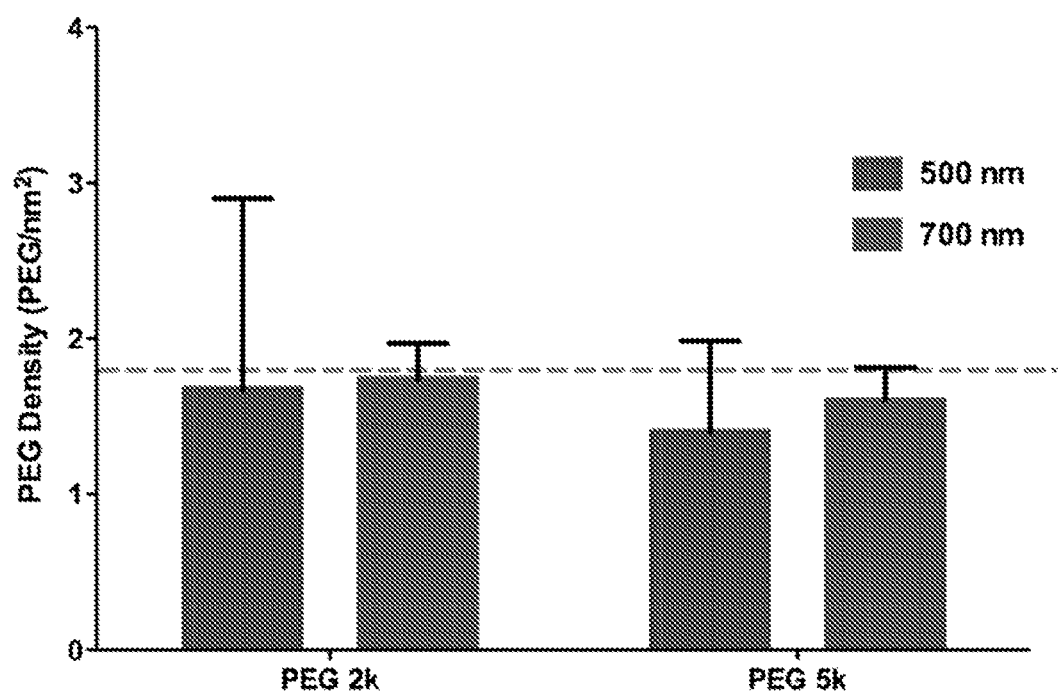
FIG. 9 includes a graph showing PEG density for 500 nm and 700 nm silica particles that have carboxyl surface functional groups and that have been grafted with $PEG_{2K}$ or $PEG_{5K}$, wherein the maximum theoretical modification is indicated by the dashed line. Carboxyl groups before and after grafting were determined using 1-pyrenyldiazomethane.

The residual carboxylic groups present on the PEGylated Si particles were quantified using PDAM, as in Example 1. The Si-PEG particles (2 μL) were diluted in 40 μL of Pluronic F127 solution (15 mg/mL) in a half-area black 96 well plate. Twenty microliters of a saturated PDAM solution (~0.3 mg/mL in methanol) were added to each well, and the PDAM and particle fluorescence intensities were measured at 340/395 and 330/340 nm, respectively, using a Spectra-Max 2 microplate reader. The sample PDAM fluorescence was compared to a standard curve of unmodified Si particles to determine the residual carboxylic group density (% COOH). The density of conjugated PEG groups (P) was calculated according to equation 1, with C=1.8 groups/nm$^2$ for the example Si particles (FIG. 9). Duplicate samples were tested per run.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

The terms "comprising", "including," and "having" are intended to be inclusive and mean that there may be additional elements other than the listed elements.

Following long-standing patent law convention, the terms "a", "an", and "the" refer to "one or more" when used in this application, including the claims. Thus, for example, reference to "a coating" includes a plurality of such eyes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

REFERENCES

Throughout this document, various references are mentioned. All such references, including those listed below, are incorporated herein by reference.

1. Cu, Y. and W. M. Saltzman, *Controlled surface modification with poly(ethylene)glycol enhances diffusion of PLGA nanoparticles in human cervical mucus.* Mol Pharm, 2009. 6(1): p. 173-81.
2. Perry, J. L., K. G. Reuter, M. P. Kai, K. P. Herlihy, S. W. Jones, J. C. Luft, M. Napier, J. E. Bear, and J. M. Desimone, *PEGylated PRINT Nanoparticles: The Impact of PEG Density on Protein Binding, Macrophage Asso-* ciation, Biodistribution, and Pharmacokinetics. Nano Lett, 2012. 12(10): p. 5304-10.
3. Jokerst, J. V., T. Lobovkina, R. N. Zare, and S. S. Gambhir, *Nanoparticle PEGylation for imaging and therapy*. Nanomedicine (Lond), 2011. 6(4): p. 715-28.
4. Lai, S. K., D. E. O'Hanlon, S. Harrold, S. T. Man, Y. Y. Wang, R. Cone, and J. Hanes, *Rapid transport of large polymeric nanoparticles in fresh undiluted human mucus*. Proc Natl Acad Sci USA, 2007. 104(5): p. 1482-7.
5. Lai, S. K., Y. Y. Wang, and J. Hanes, *Mucus-penetrating nanoparticles for drug and gene delivery to mucosal tissues*. Adv Drug Deliv Rev, 2009. 61(2): p. 158-71.
6. Nance, E. A., G. F. Woodworth, K. A. Sailor, T. Y. Shih, Q. Xu, G. Swaminathan, D. Xiang, C. Eberhart, and J. Hanes, *A dense poly(ethylene glycol) coating improves penetration of large polymeric nanoparticles within brain tissue*. Sci Transl Med, 2012. 4(149): p. 149ra119.
7. Panorchan, P., D. Wirtz, and Y. Tseng, *Structure function relationship of biological gels revealed by multiple-particle tracking and differential interference contrast microscopy: the case of human lamin networks*. Phys Rev E Stat Nonlin Soft Matter Phys, 2004. 70(4 Pt 1): p. 041906.
8. Valentine, M. T., Z. E. Perlman, T. J. Mitchison, and D. A. Weitz, *Mechanical properties of Xenopus egg cytoplasmic extracts*. Biophys J, 2005. 88(1): p. 680-9.
9. Efremova, N. V., Y. Huang, N. A. Peppas, and D. E. Leckband, *Direct Measurement of Interactions between Tethered Poly(ethylene glycol) Chains and Adsorbed Mucin Layers*. Langmuir, 2002. 18(3): p. 836-845.
10. Lele, B. S. and A. S. Hoffman, *Mucoadhesive drug carriers based on complexes of poly(acrylic acid) and PEGylated drugs having hydrolysable PEG-anhydride-drug linkages*. J. Controlled Release, 2000. 69(2): p. 237-48.
11. Serra, L., J. Domenech, and N. A. Peppas, *Design of poly(ethylene glycol)-tethered copolymers as novel mucoadhesive drug delivery systems*. Eur. J. Pharm. Biopharm., 2006. 63(1): p. 11-8.
12. Shojaei, A. H. and X. Li, *Mechanisms of buccal mucoadhesion of novel copolymers of acrylic acid and polyethylene glycol monomethylether monomethacrylate*. J. Controlled Release, 1997. 47(2): p. 151-161.
13. Yoncheva, K., S. Gomez, M. A. Campanero, C. Gamazo, and J. M. Irache, *Bioadhesive properties of pegylated nanoparticles*. Expert. Opin. Drug Delivery, 2005. 2(2): p. 205-18.
14. Levin, C. S., S. W. Bishnoi, N. K. Grady, and N. J. Halas, *Determining the conformation of thiolated poly(ethylene glycol) on Au nanoshells by surface-enhanced Raman scattering spectroscopic assay*. Anal Chem, 2006. 78(10): p. 3277-81.
15. Li, S. D. and L. Huang, *Nanoparticles evading the reticuloendothelial system: role of the supported bilayer*. Biochim Biophys Acta, 2009. 1788(10): p. 2259-66.
16. Duncanson, W. J., M. A. Figa, K. Hallock, S. Zalipsky, J. A. Hamilton, and J. Y. Wong, *Targeted binding of PLA microparticles with lipid-PEG-tethered ligands*. Biomaterials, 2007. 28(33): p. 4991-9.
17. Jokerst, J. V., Z. Miao, C. Zavaleta, Z. Cheng, and S. S. Gambhir, *Affibody-functionalized gold-silica nanoparticles for Raman molecular imaging of the epidermal growth factor receptor*. Small, 2011. 7(5): p. 625-33.
18. Wang, Y. Y., S. K. Lai, J. S. Suk, A. Pace, R. Cone, and J. Hanes, *Addressing the PEG mucoadhesivity paradox to engineer nanoparticles that "slip" through the human mucus barrier*. Angew Chem Int Ed Engl, 2008. 47(50): p. 9726-9.
19. Lieleg, O., I. Vladescu, and K. Ribbeck, *Characterization of particle translocation through mucin hydrogels*. Biophys J, 2010. 98(9): p. 1782-9.
20. Shukair, S. A., S. A. Allen, G. C. Cianci, D. J. Stieh, M. R. Anderson, S. M. Baig, C. J. Gioia, E. J. Spongberg, S. M. Kauffman, M. D. McRaven, H. Y. Lakougna, C. Hammond, P. F. Kiser, and T. J. Hope, *Human cervicovaginal mucus contains an activity that hinders HIV-1 movement*. Mucosal Immunol, 2012.
21. Mert, O., S. K. Lai, L. Ensign, M. Yang, Y. Y. Wang, J. Wood, and J. Hanes, *A poly(ethylene glycol)-based surfactant for formulation of drug-loaded mucus penetrating particles*. J Control Release, 2012. 157(3): p. 455-60.
22. Tang, B. C., M. Dawson, S. K. Lai, Y. Y. Wang, J. S. Suk, M. Yang, P. Zeitlin, M. P. Boyle, J. Fu, and J. Hanes, *Biodegradable polymer nanoparticles that rapidly penetrate the human mucus barrier*. Proc Natl Acad Sci USA, 2009. 106(46): p. 19268-73.
23. Yang, M., S. K. Lai, Y. Y. Wang, W. Zhong, C. Happe, M. Zhang, J. Fu, and J. Hanes, *Biodegradable nanoparticles composed entirely of safe materials that rapidly penetrate human mucus*. Angew Chem Int Ed Engl, 2011. 50(11): p. 2597-600.
24. Yu, T., Y.-Y. Wang, M. Yang, C. Schneider, W. Zhong, S. Pulicare, W.-J. Choi, O. Mert, J. Fu, S. Lai, and J. Hanes, *Biodegradable mucus penetrating nanoparticles composed of diblock copolymers of polyethylene glycol and poly(lactic-<i>co</i>-glycolic acid)*. Drug Delivery and Translational Research, 2012. 2(2): p. 124-128.
25. Butterworth, M. D., L. Illum, and S. S. Davis, *Preparation of ultrafine silica-and PEG-coated magnetite particles*. Colloids and Surfaces A: Physicochemical and Engineering Aspects, 2001. 179(1): p. 93-102.
26. Kim, S., Y. T. Lim, E. G. Soltesz, A. M. De Grand, J. Lee, A. Nakayama, J. A. Parker, T. Mihaljevic, R. G. Laurence, D. M. Dor, L. H. Cohn, M. G. Bawendi, and J. V. Frangioni, *Near-infrared fluorescent type II quantum dots for sentinel lymph node mapping*. Nat Biotechnol, 2004. 22(1): p. 93-7.
27. Moghimi, M. and S. M. Moghimi, *Lymphatic targeting of immuno-PEG-liposomes: evaluation of antibody-coupling procedures on lymph node macrophage uptake*. J Drug Target, 2008. 16(7): p. 586-90.
28. Oussoren, C. and G. Storm, *Liposomes to target the lymphatics by subcutaneous administration*. Adv Drug Deliv Rev, 2001. 50(1-2): p. 143-56.
29. Carter, C. L., C. Allen, and D. E. Henson, *Relation of tumor size, lymph node status, and survival in 24,740 breast cancer cases*. Cancer, 1989. 63(1): p. 181-7.
30. Chambers, A. F., A. C. Groom, and I. C. MacDonald, *Dissemination and growth of cancer cells in metastatic sites*. Nat Rev Cancer, 2002. 2(8): p. 563-72.
31. Kojima, T., Y. Watanabe, Y. Hashimoto, S. Kuroda, Y. Yamasaki, S. Yano, M. Ouchi, H. Tazawa, F. Uno, S. Kagawa, S. Kyo, H. Mizuguchi, Y. Urata, N. Tanaka, and T. Fujiwara, *In vivo biological purging for lymph node metastasis of human colorectal cancer by telomerase-specific oncolytic virotherapy*. Ann Surg, 2010. 251(6): p. 1079-86.
32. Garcia-Fuentes, M., D. Torres, M. Martin-Pastor, and M. J. Alonso, *Application of NMR spectroscopy to the characterization of PEG-stabilized lipid nanoparticles*. Langmuir, 2004. 20(20): p. 8839-45.

33. Nimura, N., T. Kinoshita, T. Yoshida, A. Uetake, and C. Nakai, *1-Pyrenyldiazomethane as a fluorescent labeling reagent for liquid chromatographic determination of carboxylic acids*. Anal Chem, 1988. 60(19): p. 2067-70.
34. Jia, Z. and C. Tian, *Quantitative determination of polyethylene glycol with modified Dragendorff reagent method*. Desalination, 2009. 247(1-3): p. 423-429.
35. Merkel, T. J., S. W. Jones, K. P. Herlihy, F. R. Kersey, A. R. Shields, M. Napier, J. C. Luft, H. Wu, W. C. Zamboni, A. Z. Wang, J. E. Bear, and J. M. DeSimone, *Using mechanobiological mimicry of red blood cells to extend circulation times of hydrogel microparticles*. Proc Natl Acad Sci USA, 2011. 108(2): p. 586-91.
36. Geng, Y., P. Dalhaimer, S. Cai, R. Tsai, M. Tewari, T. Minko, and D. E. Discher, *Shape effects of filaments versus spherical particles in flow and drug delivery*. Nat Nanotechnol, 2007. 2(4): p. 249-55.
37. Mitragotri, S. and J. Lahann, *Physical approaches to biomaterial design*. Nat Mater, 2009. 8(1): p. 15-23.
38. Rizzo, V. and V. Pinciroli, *Quantitative NMR in synthetic and combinatorial chemistry*. J Pharm Biomed Anal, 2005. 38(5): p. 851-7.
39. Skoog, B., *Determination of polyethylene glycols 4000 and 6000 in plasma protein preparations*. Vox Sang, 1979. 37(6): p. 345-9.
40. Daigneault, M., J. A. Preston, H. M. Marriott, M. K. Whyte, and D. H. Dockrell, *The identification of markers of macrophage differentiation in PMA-stimulated THP-1 cells and monocyte-derived macrophages*. PLoS One, 2010. 5(1): p. e8668.
41. Lai, S. K., K. Hida, S. T. Man, C. Chen, C. Machamer, T. A. Schroer, and J. Hanes, *Privileged delivery of polymer nanoparticles to the perinuclear region of live cells via a non-clathrin, non-degradative pathway*. Biomaterials, 2007. 28(18): p. 2876-84.
42. S. I. Jeon, L. H. Lee, J. D. Andrade, P. G. De Gennes, *J Colloid Interf Sci* 1991, 142, 149-158.
43. A. J. Pertsin, M. Grunze, *Langmuir: the ACS journal of surfaces and colloids* 2000, 16, 8829-8841.
44. S. Sharma, R. W. Johnson, T. A. Desai, *Biosensors & bioelectronics* 2004, 20, 227-239.
45. D. Needham, T. J. McIntosh, D. D. Lasic, *Biochimica et biophysica acta* 1992, 1108, 40-48.
46. D. D. Lasic, F. J. Martin, A. Gabizon, S. K. Huang, D. Papahadjopoulos, *Biochimica et biophysica acta* 1991, 1070, 187-192.
47. M. C. Woodle, D. D. Lasic, *Biochimica et biophysica acta* 1992, 1113, 171-199.
48. C. D. Walkey, J. B. Olsen, H. Guo, A. Emili, W. C. Chan, *Journal of the American Chemical Society* 2012, 134, 2139-2147.
49. A. S. Zahr, C. A. Davis, M. V. Pishko, *Langmuir: the ACS journal of surfaces and colloids* 2006, 22, 8178-8185.
50. T. M. Allen, C. Hansen, F. Martin, C. Redemann, A. Yau-Young, *Biochimica et biophysica acta* 1991, 1066, 29-36
51. A. L. Klibanov, K. Maruyama, V. P. Torchilin, L. Huang, *FEBS Lett* 1990, 268, 235-237.
52. J. Senior, C. Delgado, D. Fisher, C. Tilcock, G. Gregoriadis, *Biochimica et biophysica acta* 1991, 1062, 77-82.
53. P. G. de Gennes, *Macromolecules* 1980, 13, 1069-1075.
54. V. B. Damodaran, C. J. Fee, T. Ruckh, K. C. Popat, *Langmuir: the ACS journal of surfaces and colloids* 2010, 26, 7299-7306.
55. S. J. Budijono, B. Russ, W. Saad, D. H. Adamson, R. K. Prud'homme, *Colloids and Surfaces A: Physicochemical and Engineering Aspects* 2010, 360, 105-110.
56. M. C. Woodle, K. K. Matthay, M. S. Newman, J. E. Hidayat, L. R. Collins, C. Redemann, F. J. Martin, D. Papahadjopoulos, *Biochimica et biophysica acta* 1992, 1105, 193-200.
57. A. Mori, A. L. Klibanov, V. P. Torchilin, L. Huang, *FEBS Lett* 1991, 284, 263-266.
58. E. Fattal, H. Hillaireau, M. Simona, J. Nicolas, N. Tsapis, in *Fundamentals and Applications of Controlled Release Drug Delivery* (Eds.: J. Siepmann, R. A. Siegel, M. J. Rathbone), Springer US, 2012, pp. 255-288.
59. O. Lunov, T. Syrovets, C. Loos, J. Beil, M. Delacher, K. Tron, G. U. Nienhaus, A. Musyanovych, V. Mailander, K. Landfester, T. Simmet, *ACS nano* 2011, 5, 1657-1669.
60. C. Jeppesen, J. Y. Wong, T. L. Kuhl, J. N. Israelachvili, N. Mullah, S. Zalipsky, C. M. Marques, *Science* 2001, 293, 465-468.
61. S. K. Lai, Y. Y. Wang, K. Hida, R. Cone, J. Hanes, Proceedings of the National Academy of Sciences of the United Stated of America 2010, 107, 598-603

What is claimed is:

1. A composition, comprising:
    a particle;
    a plurality of surface functional groups on a surface of the particle; and
    a plurality of coating polymers bound to the surface functional groups and forming a coating on the particle that includes a density ratio of about 1.0 to about 20.0, the density ratio being equal to a Flory radius of the plurality of coating polymers divided by a distance between adjacent surface functional groups;
    wherein the surface functional groups are selected from the group consisting of carboxyl, amine, aldehyde, acetal, thiol, acrylate, isocyanate, maleimide, hydroxyl, halogen, electrostatically charged functional groups, and combinations thereof.

2. The composition of claim 1, wherein the density ratio is about 2.8 to about 10.0.

3. The composition of claim 1, wherein the particle is a nanoparticle, a microparticle, or a combination thereof.

4. The composition of claim 3, wherein the particle having a diameter of about 5 nm to about 500 nm.

5. The composition of claim 1, wherein the particle is comprised of a polymer.

6. The composition of claim 1, wherein the particle is polystyrene, silica, or combinations thereof.

7. The composition of claim 1, wherein the plurality of coating polymers is a hydrophilic polymer.

8. The composition of claim 7, wherein the hydrophilic polymer is poly(ethylene glycol) (PEG).

9. The composition of claim 1, wherein the plurality of coating polymers have a molecular weight of about 100 g/mol to about 20,000 g/mol.

10. The composition of claim 9, wherein the plurality of coating polymers have a molecular weight of about 100 g/mol to about 5,000 g/mol.

11. The composition of claim 1, wherein the plurality of coating polymers is a functional group that can react and form a bond with the surface functional groups.

12. The composition of claim 11, wherein the functional groups on the plurality of coating polymers are selected from carboxyl, amine, aldehyde, acetal, thiol, acrylate, isocyanate, maleimide, hydroxyl, halogen, and combinations thereof.

13. The composition of claim 11, wherein the functional groups on the plurality of coating polymers are on a terminal end of the coating polymers.

14. The composition of claim 1, wherein the surface functional groups are selected from carboxyl, amine, aldehyde, acetal, thiol, acrylate, isocyanate, maleimide, hydroxyl, halogen, and combinations thereof.

15. The composition of claim 1, wherein the particle further comprises a bioactive agent.

16. The composition of claim 1, wherein the composition comprises a plurality of the particles.

17. A method for making a particle, comprising:
providing a particle that includes surface functional groups on the surface of the particle; and
contacting the surface functional groups of the particle with a plurality of coating polymers to form a coating on the particle that includes a density ratio of about 1.0 to about 20.0, the density ratio being equal to a Flory radius of the plurality of coating polymers divided by a distance between adjacent surface functional groups;
wherein the surface functional groups are selected from the group consisting of carboxyl, amine, aldehyde, acetal, thiol, acrylate, isocyanate, maleimide, hydroxyl, halogen, electrostatically charged functional groups, and combinations thereof.

* * * * *